(12) United States Patent
Zhang et al.

(10) Patent No.: US 6,899,948 B2
(45) Date of Patent: May 31, 2005

(54) DENTAL MATERIALS WITH NANO-SIZED SILICA PARTICLES

(75) Inventors: Xiaodong Zhang, Woodbury, MN (US); Brant Ulrick Kolb, Afton, MN (US); Douglas Alan Hanggi, Woodbury, MN (US); Bradley Dene Craig, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 62 days.

(21) Appl. No.: 10/122,767

(22) Filed: Apr. 15, 2002

(65) Prior Publication Data

US 2002/0156152 A1 Oct. 24, 2002

Related U.S. Application Data

(62) Division of application No. 09/428,937, filed on Oct. 28, 1999, now abandoned.

(51) Int. Cl.[7] .................................................. B32B 5/16
(52) U.S. Cl. ........................ 428/331; 428/405; 428/407; 427/220; 427/372.2
(58) Field of Search ................................. 428/405, 407, 428/331, 403, 404; 427/372.2, 220

(56) References Cited

U.S. PATENT DOCUMENTS

| | | | |
|---|---|---|---|
| 2,984,628 A | 5/1961 | Alexander et al. |
| 3,018,262 A | 1/1962 | Schroeder |
| 3,066,112 A | 11/1962 | Bowen |
| 3,117,099 A | 1/1964 | Proops et al. |
| 3,179,623 A | 4/1965 | Bowen |
| 3,194,784 A | 7/1965 | Bowen |
| 3,442,817 A | 5/1969 | Luebke |
| 3,514,252 A | 5/1970 | Levy, Jr. et al. |
| 3,539,533 A | 11/1970 | Lee et al. |
| 3,629,187 A | 12/1971 | Waller |
| 3,708,296 A | 1/1973 | Schlesinger |
| 3,709,706 A | 1/1973 | Sowman |
| 3,709,866 A | 1/1973 | Waller |
| 3,729,313 A | 4/1973 | Smith |
| 3,741,769 A | 6/1973 | Smith |
| 3,751,399 A | 8/1973 | Lee et al. |
| 3,766,132 A | 10/1973 | Lee et al. |
| 3,808,006 A | 4/1974 | Smith |
| 3,860,556 A | 1/1975 | Taylor |
| 3,926,906 A | 12/1975 | Lee, II et al. |

(Continued)

FOREIGN PATENT DOCUMENTS

| | | |
|---|---|---|
| CA | 2074128 | 1/1993 |
| CA | 2202732 | 10/1997 |

(Continued)

OTHER PUBLICATIONS

Decker; "Photoinitiated Curing of Multifunctional Monomers," *Chimia*, vol. 47, pp. 378–382 (1993).
Patent Absracts of Japan, Nov. 28, 1997; 1997(11); and JP 09/194674A, Jul. 29, 1997 (abstract).

(Continued)

*Primary Examiner*—H. Thi Le
(74) *Attorney, Agent, or Firm*—Sean Edman

(57) ABSTRACT

A dental material comprising a hardenable resin and silica particles dispersed within the hardenable resin, wherein the silica particles have an average diameter of less than about 200 nm and are present in an amount greater than about 40 wt % of the weight of the dental material. The dental material may further comprise a heavy metal oxide. The dental material can be used as dental adhesives, artificial crowns, anterior or posterior fillings, casting materials, cavity liners, cements, coating compositions, mill blanks, orthodontic devices, restoratives, prostheses, and sealants.

28 Claims, 1 Drawing Sheet

—— 0.1 μm

U.S. PATENT DOCUMENTS

| Patent No. | | Date | Inventor(s) | |
|---|---|---|---|---|
| 4,002,669 A | | 1/1977 | Gross et al. | |
| 4,027,073 A | * | 5/1977 | Clark | 428/412 |
| 4,069,055 A | | 1/1978 | Crivello | |
| 4,071,424 A | | 1/1978 | Dart et al. | |
| 4,115,346 A | | 9/1978 | Gross et al. | |
| 4,150,012 A | | 4/1979 | Joos | |
| 4,216,288 A | | 8/1980 | Crivello | |
| 4,250,053 A | | 2/1981 | Smith | |
| 4,250,311 A | | 2/1981 | Crivello | |
| 4,259,117 A | | 3/1981 | Yamauchi et al. | |
| 4,292,029 A | | 9/1981 | Craig et al. | |
| 4,308,190 A | | 12/1981 | Walkowiak et al. | |
| 4,327,014 A | | 4/1982 | Kawahara et al. | |
| 4,374,937 A | | 2/1983 | Nemcek et al. | |
| 4,379,695 A | | 4/1983 | Orlowski et al. | |
| 4,387,240 A | | 6/1983 | Berg | |
| 4,389,497 A | | 6/1983 | Schmitt et al. | |
| 4,394,403 A | | 7/1983 | Smith | |
| 4,404,150 A | | 9/1983 | Tsunekawa et al. | |
| 4,427,799 A | | 1/1984 | Orlowski et al. | |
| 4,427,823 A | | 1/1984 | Inagaki et al. | |
| 4,442,240 A | | 4/1984 | Suh | |
| 4,491,508 A | | 1/1985 | Olson et al. | |
| 4,503,169 A | | 3/1985 | Randklev | |
| 4,512,743 A | | 4/1985 | Santucci et al. | |
| 4,544,359 A | | 10/1985 | Waknine | |
| 4,545,924 A | | 10/1985 | Ritter, II | |
| 4,547,531 A | | 10/1985 | Waknine | |
| 4,552,906 A | | 11/1985 | Podszûn et al. | |
| 4,612,138 A | | 9/1986 | Keiser | |
| 4,617,327 A | | 10/1986 | Podszun | |
| 4,619,817 A | | 10/1986 | Stambaugh et al. | |
| 4,629,746 A | | 12/1986 | Michl et al. | |
| 4,642,126 A | | 2/1987 | Zador et al. | |
| 4,649,165 A | | 3/1987 | Kuhlmann | |
| 4,652,274 A | | 3/1987 | Boettcher et al. | |
| 4,661,540 A | | 4/1987 | Le et al. | |
| 4,696,955 A | | 9/1987 | Kuhlmann | |
| 4,719,091 A | | 1/1988 | Wusirika | |
| 4,737,593 A | | 4/1988 | Ellrich et al. | |
| 4,746,685 A | | 5/1988 | Masuhara et al. | |
| 4,769,351 A | | 9/1988 | Soumiya et al. | |
| 4,772,511 A | | 9/1988 | Wood et al. | |
| 4,772,530 A | | 9/1988 | Gottschalk et al. | |
| 4,778,671 A | | 10/1988 | Wusirika | |
| 4,781,940 A | * | 11/1988 | Denton, Jr. | 427/2.14 |
| 4,784,794 A | | 11/1988 | Kato | |
| 4,792,577 A | | 12/1988 | Chen et al. | |
| 4,859,716 A | | 8/1989 | Ibsen et al. | |
| 4,868,288 A | | 9/1989 | Meier | |
| 4,874,450 A | | 10/1989 | Gottschalk | |
| 4,885,332 A | | 12/1989 | Bilkadi | |
| 4,886,624 A | | 12/1989 | Gradeff et al. | |
| 4,923,905 A | | 5/1990 | Masuhara et al. | |
| 4,927,560 A | | 5/1990 | Osaka et al. | |
| 4,931,414 A | | 6/1990 | Wood et al. | |
| 4,933,202 A | | 6/1990 | Rheinberger et al. | |
| 4,946,665 A | | 8/1990 | Recasens et al. | |
| 4,954,414 A | | 9/1990 | Adair et al. | |
| 4,985,229 A | | 1/1991 | Obitsu et al. | |
| 4,985,340 A | | 1/1991 | Palazzotto et al. | |
| 5,013,585 A | * | 5/1991 | Shimizu et al. | 427/220 |
| 5,037,579 A | | 8/1991 | Matchett | |
| 5,055,372 A | | 10/1991 | Shanklin et al. | |
| 5,057,393 A | | 10/1991 | Shanklin et al. | |
| 5,073,476 A | | 12/1991 | Meier et al. | |
| 5,084,586 A | | 1/1992 | Farooq | |
| 5,089,536 A | | 2/1992 | Palazzotto | |
| 5,124,417 A | | 6/1992 | Farooq | |
| 5,126,394 A | | 6/1992 | Revis et al. | |
| 5,132,337 A | | 7/1992 | Panster et al. | |
| 5,137,448 A | | 8/1992 | Dougherty et al. | |
| 5,177,120 A | | 1/1993 | Hare et al. | |
| 5,190,583 A | | 3/1993 | Menzel et al. | |
| 5,192,815 A | | 3/1993 | Okada et al. | |
| 5,219,899 A | | 6/1993 | Panster et al. | |
| 5,234,870 A | | 8/1993 | Osaka et al. | |
| 5,248,706 A | | 9/1993 | Panster et al. | |
| 5,275,759 A | | 1/1994 | Osaka et al. | |
| 5,276,068 A | | 1/1994 | Waknine | |
| 5,318,999 A | | 6/1994 | Mitra et al. | |
| 5,332,429 A | | 7/1994 | Mitra et al. | |
| 5,332,779 A | | 7/1994 | Mohri et al. | |
| 5,350,782 A | | 9/1994 | Sasaki et al. | |
| 5,401,528 A | | 3/1995 | Schmidt | |
| 5,444,104 A | | 8/1995 | Waknine | |
| 5,449,703 A | | 9/1995 | Mitra et al. | |
| 5,460,701 A | | 10/1995 | Parker et al. | |
| 5,470,910 A | | 11/1995 | Spanhel et al. | |
| 5,502,087 A | | 3/1996 | Tateosian et al. | |
| 5,545,676 A | | 8/1996 | Palazzotto et al. | |
| 5,558,849 A | | 9/1996 | Sharp | |
| 5,593,781 A | | 1/1997 | Nass et al. | |
| 5,609,675 A | | 3/1997 | Noritake et al. | |
| 5,643,497 A | | 7/1997 | Kaga et al. | |
| 5,648,407 A | | 7/1997 | Goetz et al. | |
| 5,658,376 A | | 8/1997 | Noguchi et al. | |
| 5,698,483 A | | 12/1997 | Ong et al. | |
| 5,750,258 A | * | 5/1998 | Sakai et al. | 428/405 |
| 5,760,126 A | | 6/1998 | Engle et al. | |
| 5,776,239 A | | 7/1998 | Bruno | |
| 5,820,978 A | * | 10/1998 | Huang | 428/331 |
| 5,830,242 A | | 11/1998 | Yao | |
| 5,846,310 A | * | 12/1998 | Noguchi et al. | 106/482 |
| 5,856,373 A | | 1/1999 | Kaisaki et al. | |
| 5,879,715 A | | 3/1999 | Higgins et al. | |
| 5,886,069 A | | 3/1999 | Bolt | |
| 5,935,275 A | | 8/1999 | Burgard et al. | |
| 5,936,006 A | | 8/1999 | Rheinberger et al. | |
| 5,942,559 A | | 8/1999 | Voser et al. | |
| 5,985,168 A | | 11/1999 | Phule | |
| 6,025,406 A | | 2/2000 | Oxman et al. | |
| 6,030,606 A | | 2/2000 | Holmes | |
| 6,136,886 A | | 10/2000 | Deguchi | |
| 6,210,790 B1 | * | 4/2001 | Crivello | 428/325 |
| 6,245,872 B1 | | 6/2001 | Frey et al. | |
| 6,302,926 B1 | | 10/2001 | Anselmann et al. | |
| 6,376,590 B2 | | 4/2002 | Kolb et al. | |
| 6,387,981 B1 | | 5/2002 | Zhang et al. | |
| 6,399,037 B1 | | 6/2002 | Pflug et al. | |
| 6,413,638 B1 | * | 7/2002 | Mager et al. | 428/403 |
| 6,417,246 B1 | | 7/2002 | Jia et al. | |
| 6,572,693 B1 | * | 6/2003 | Wu et al. | 106/35 |
| 6,586,483 B2 | * | 7/2003 | Kolb et al. | 521/91 |
| 6,693,143 B2 | * | 2/2004 | Pflug | 523/116 |

FOREIGN PATENT DOCUMENTS

| | | |
|---|---|---|
| DE | 693 14 374 T2 | 10/1993 |
| DE | 195 24 362 A1 | 1/1996 |
| DE | 195 08 586 C2 | 9/1996 |
| DE | 195 40 623 A1 | 5/1997 |
| EP | 0 173 567 | 3/1986 |
| EP | 0 184 467 A2 | 6/1986 |
| EP | 0 094 914 | 9/1986 |
| EP | 0 315 186 A3 | 5/1989 |
| EP | 0 315 186 A2 | 5/1989 |
| EP | 0 368 657 A3 | 5/1990 |
| EP | 0 368 657 A2 | 5/1990 |
| EP | 0 434 334 | 6/1991 |
| EP | 0 530 926 | 3/1993 |
| EP | 0 315 186 B1 | 4/1993 |

| | | |
|---|---|---|
| EP | 0 368 657 B1 | 8/1993 |
| EP | 0 565 403 A1 | 10/1993 |
| EP | 0 712 912 A2 | 5/1996 |
| EP | 0 732 099 | 9/1996 |
| EP | 0 565 403 B1 | 10/1997 |
| EP | 0 841 304 A1 | 5/1998 |
| GB | 1 596 241 | 8/1981 |
| GB | 2310855 | 9/1997 |
| JP | 54 07776 A | 6/1979 |
| JP | 58079818 A | 11/1981 |
| JP | 58135131 A | 2/1982 |
| JP | 59107969 A | 12/1982 |
| JP | 60103033 A | 11/1983 |
| JP | 60137827 A | 12/1983 |
| JP | 60176920 A | 2/1984 |
| JP | 60255622 A | 5/1984 |
| JP | 3-46407 | 6/1984 |
| JP | 61141620 A | 12/1984 |
| JP | 61227917 A | 4/1985 |
| JP | 61270217 A | 5/1985 |
| JP | 4-72768 | 9/1985 |
| JP | 62065932 A | 9/1985 |
| JP | 62091421 A | 10/1985 |
| JP | 62128924 A | 11/1985 |
| JP | 62212224 A | 3/1986 |
| JP | 62226815 A | 3/1986 |
| JP | 63002809 A | 6/1986 |
| JP | 1076919 A | 9/1987 |
| JP | 1079015 A | 9/1987 |
| JP | 1083518 A | 9/1987 |
| JP | 1083519 A | 9/1987 |
| JP | 1083520 A | 9/1987 |
| JP | 1176225 A | 12/1987 |
| JP | 2137729 A | 11/1988 |
| JP | 2137730 A | 11/1988 |
| JP | 2137731 A | 11/1988 |
| JP | 2137732 A | 11/1988 |
| JP | 3174326 A | 12/1989 |
| JP | 4031307 A | 5/1990 |
| JP | 4089319 A | 8/1990 |
| JP | 7118016 A | 10/1993 |
| JP | 6-191827 | 7/1994 |
| JP | 7-17820 | 1/1995 |
| JP | 8277114 A | 4/1995 |
| JP | 7-291817 | 11/1995 |
| JP | 9235119 A | 3/1996 |
| JP | 08-311115 | 11/1996 |
| JP | 9-194674 | 7/1997 |
| WO | WO 93/05875 | 4/1993 |
| WO | WO 98/13008 | 4/1998 |
| WO | WO 99/17716 | 4/1999 |
| WO | WO 99/65453 | 12/1999 |
| WO | WO 00/03688 | 1/2000 |
| WO | WO 00/20494 | 4/2000 |
| WO | WO 01/30307 A1 | 5/2001 |

OTHER PUBLICATIONS

Blumenthal, "The Chemical Behavior of Zirconium," Van Nostrand Company, Princeton, NJ: 311–338.

Burgard et al., "Routes to Deagglomerated Nanopowder by Chemical Synthesis," *Mat. Res. Soc. Symp. Proc.*, 1994;324:101–107.

Burgard et al., "Synthesis and Colloidal Processing of Nanocrystalline (Y2O3–Stabilized) ZrO2 Powders by a Surface Free Energy Controlled Process," *Mat. Res. Soc. Symp. Proc.*, 1997;432:113–121.

Cabot Corporation product brochure, "Cab–o–Sil® Untreated Fumed Silica Properties and Functions," 1978. Title page, Publication p., 3–5.

Chatry et al., "The Role of Complexing Ligands in the Formation of Non–Aggregated Nanoparticles of Zirconia," *Journal of Sol–Gel Science and Technology*, 1994;1:233–240.

Craig, "Restorative Dental Materials," 8$^{th}$ ed., 1989: 256–257.

Definition of "binary compound," Oct. 9, 1997, Retrieved from the On–line Medical Dictionary on Jun. 6, 2002 at <http://cancerweb.ncl.ac.uk/cgi–bin/omd?binary+compound> 1 pg.

Definition of "oxide," Oct. 9, 1997, Retrieved from the On–line Medical Dictionary on Jun. 6, 2002 at <http://cancerweb.ncl.ac.uk/cgi–bin/omd?oxide> 1 pg.

"Determination of Polymerization Shrinkage Kinetics in Visible–Light–Cured Materials: Methods of Development," *Dental Materials*, Oct. 1991;281–286.

Degussa AG product brochure, "Technical Bulletin Pigments, AEROSIL® as a Thickening Agent for Liquid Systems, No. 23," Jul. 1989; Title page, Publication p., 3–29.

Degussa AG product brochure, "Technical Bulletin Pigments, AEROSIL® in Pharmaceuticals and Cosmetics, No. 49," Sep. 1997; Title page, Publication p., 5–6.

Grant, *Grant and Hackh's Chemical Dictionary*, 5$^{th}$ Edition, Title Page, Publication p., 1987: 106 and 231.

Lee et al., *Handbood of Epoxy Resins*, McGraw–Hill Book Co., New York 1967; cover page, title page and table of contents only.

Macosko, "Rheology Principles, Measurements, and Applications," VCH Publishers, Inc., New York, 1994: 92–98.

Matijevic, *Surface & Colloid Science*, vol. 6, ed. Wiley Interscience, 1973:23–29.

"Perthometer, Surface Texture Parameters," Mahr GMB, Gottingen, Germany ed. Sep. 1999 1:10.

* cited by examiner

DENTAL MATERIALS WITH NANO-SIZED SILICA PARTICLES

This is a division of application Ser. No. 09/428,937, filed 28 Oct. 1999, which is incorporated herein by reference, now abandoned.

FIELD OF THE INVENTION

The invention relates broadly to dental materials containing nano-sized particles dispersed in a hardenable resin. These materials can be used as restoratives, adhesives, cements, orthodontic devices, mill blanks and prostheses. More specifically, the invention relates to dental materials containing discrete, nano-sized silica particles that impart high strength and high translucency to the dental materials.

BACKGROUND

Dental materials generally have unique requirements as compared to the broad spectrum of composite materials. For health reasons, dental materials should be suitable for use in the oral environment. In certain instances, strength and durability of a dental material is important to ensure satisfactory performance. For example, in dental work that is performed at dentition locations where mastication forces are generally great, high strength and durability is desirable. In other instances, aesthetic character or quality (e.g., luster and translucency) is highly desired. This is often the case where dental work is performed at locations where a tooth repair or restoration can be seen from a relatively short distance.

Strength in a dental material is typically achieved by adding fillers. Generally, a dental material possessing greater mechanical strength characteristics is filled or loaded with larger sized particles; i.e particles having a diameter greater than about 0.4 micrometers. These materials are often referred to as hybrid composites. A disadvantage to these composites, however, is their tendency to lack luster and aesthetic character. Another disadvantage of composites with large-sized particles is that with repeated toothbrushing (a requirement for oral hygiene), the hardened resin can wear away, exposing the large filler particles and leave a dull, unaesthetic surface. This can subsequently lead to plaque accumulation.

Increasing filler levels can also increase the strength of a dental material. However, this can lead to increased visual opacity, thereby reducing translucency and aesthetic quality.

Canadian Patent Application 2,202,732 teaches polymerizable dental materials comprising a sol of surface modified silica particles in a liquid, organic dispersion agent. The silica particles comprise about 35 wt % of the dental material.

Good rheological properties in unhardened dental materials are advantageous to a dental practitioner. This allows the practitioner to easily manipulate and place the material in its desired location and achieve proper contact and anatomical form before hardening or curing. Nanometer sized ("nano-sized") silica particles, most often in the form of fumed silica, have been dispersed in polymerizable dental resins. A fumed silica material available from DeGussa, under the trade designation OX-50 (DeGussa AG, Hanau, Germany), has had widespread use. Materials made with fumed silica dispersed at high loading levels within the resins, however, result in dilatant compositions that are generally impractical for dental practice. A well-recognized dental reference book by Craig, entitled, "Restorative Dental Materials," 8$^{th}$ ed., 1989 teaches that highly-loaded fumed silica materials generally provide materials with poor theological properties. (See e.g., p.256 of Craig.) Thus, conventional materials whose concentrations of an inorganic component (particles) are adjusted for a desired strength, typically result in undesirably dilatant materials.

It has also been the practice to incorporate pre-polymerized particles to overcome the dilatant rheology. These, however, can result in low strength materials.

It is generally desired that the dental material blends well with the surrounding dentition and looks life-like. Aesthetic quality in dental materials is typically achieved by creating material that has tooth-like colors/shades. "Microfills," a certain class of dental materials, tend to have good luster to better replicate tooth appearance. One example of a "microfill" is commercially available under the trade designation SILUX PLUS (3M Co., St. Paul, Minn.). Microfills, however, generally have less mechanical strength than hybrid composites or "macrofills."

Thus, in current practice, for applications where high strength and high aesthetic quality are desired, a practitioner is typically required to first use an underlying foundation of a material possessing high physical strength followed by an overlying layer of a microfill. It would be advantageous to provide a single material that possesses high strength and high aesthetic quality.

SUMMARY OF THE INVENTION

The invention provides a dental material comprising a hardenable resin and nano-sized silica particles dispersed within the resin to provide strong, translucent dental materials. The silica particles have an average diameter of less than about 200 nm and are present in an amount that is greater than about 40 wt % of the total weight of the dental material.

"Hardenable" is descriptive of a material that can be cured or solidified e.g., by heating to remove solvent, heating to cause polymerization, chemical crosslinking, radiation-induced polymerization or crosslinking, or the like.

"Dispersed within the resin" means that silica particles are present in the resin as discrete, unassociated (i.e. non-agglomerated and non-aggregated) particles.

The dental material of the invention can be used as dental adhesives, artificial crowns, anterior or posterior fillings, casting materials, cavity liners, cements, coating compositions, mill blanks, orthodontic devices, restoratives, prostheses, and sealants.

In one aspect of the invention, the hardenable resin can be an acrylate, methacrylate, or epoxy or combinations thereof.

In a further aspect of the invention, a heavy metal can be included in the dental material to impart radiopacity.

Methods of using the dental material are also provided, comprising the steps of placing the dental material near or on a tooth surface, changing the topography of the material and hardening the material.

DETAILED DESCRIPTION OF THE PREFERRED EMBODIMENTS

Figure 1:
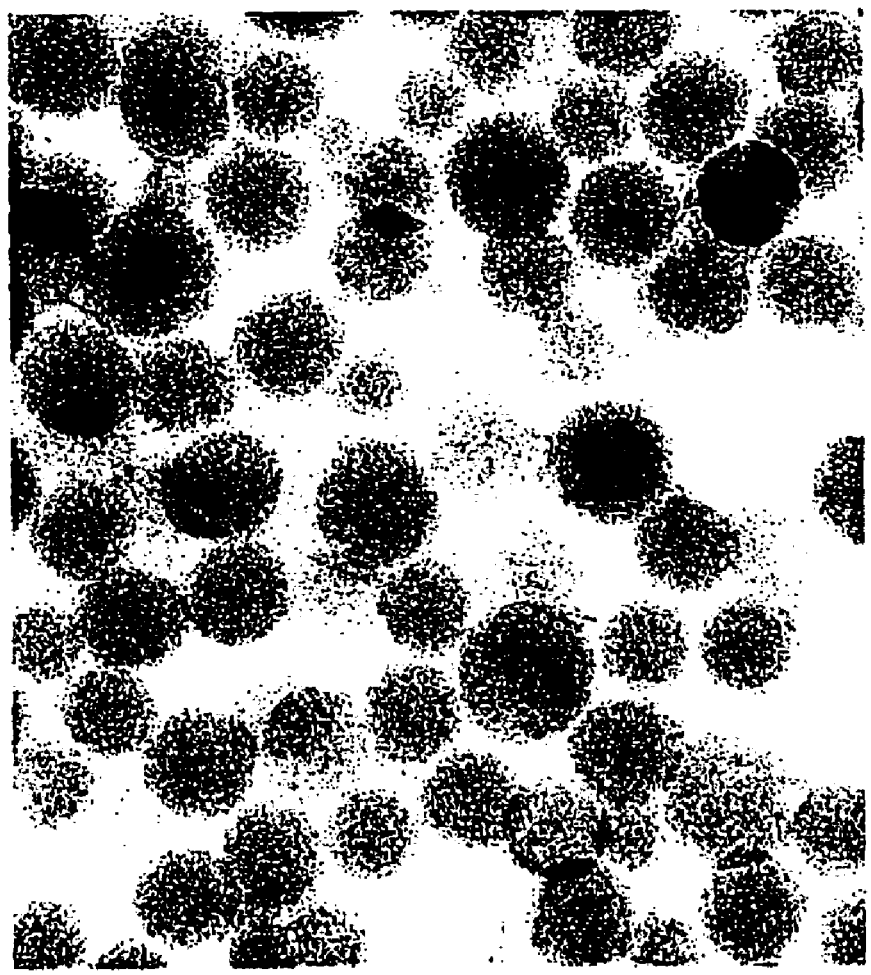
FIG. 1 is a digital image of a TEM (transmission electron micrograph) of a preferred embodiment of a dental material of the invention, taken at 300,000× magnification.

The present invention provides dental materials having a hardenable resin and nano-sized (i.e., less than 200 nm average diameter) silica filler dispersed within the resin. The silica filler is present in an amount that yields both high strength and high translucency. Optionally, a heavy metal oxide can be included in the material to provide radiopacity to the material.

The dental materials of the present invention can be used for example, as dental adhesives, artificial crowns, anterior or posterior fillings, casting materials, cavity liners, cements, coating compositions, mill blanks, orthodontic devices, restoratives, prostheses, and sealants. In a preferred aspect, the dental material is a dental restorative. The restoratives of the invention can be placed directly in the mouth and cured (hardened) in situ, or alternatively, may be fabricated into a prosthesis outside the mouth and subsequently adhered in place inside the mouth.

Dental materials of the present invention can be chemically curable, heat curable or light curable compositions. Light curable materials should have an appropriate initiator system. Chemically curable materials can be auto-cured (e.g. via redox initiators). Alternatively, the materials of the invention can be hardened by a combination of auto- and light-cure.

It has been found that loading a dental material with nano-sized silica particles imparts high strength as well as high translucency. Dental materials containing specified amounts of nano-sized silica particles of the present invention have especially desirable handling (Theological) properties in an unhardened state and exceptionally high strength in a hardened state coupled with good aesthetic characteristics.

Strength can be characterized by mechanical measurements such as compressive strength and diametral tensile strength. High compressive strength in a dental material is advantageous due to the forces exerted by mastication on dental repairs, replacements and restorations. Diametral tensile strength (DTS) indicates the dental material's ability to withstand compression forces that introduce a tensile stress in the material. Tests for each strength measurement are set out below in the Examples.

The dental materials of the invention, when hardened, preferably have a compressive strength of at least about 35 MPa; more preferably, the materials have a compressive strength of at least about 200 MPa; most preferably; the materials have a compressive strength of at least about 350 MPa.

Hardened dental materials of the invention preferably have a diametral tensile strength of at least about 15 MPa; more preferably at least about 40 MPa; most preferably at least about 60 MPa.

Aesthetic quality of a dental material, although a somewhat subjective characteristic (yet well-understood in the dental industry), can be preferably quantified in one aspect, by a visual opacity measurement. Visual opacity is indicative of dental material's level of translucency—low visual opacity is desired so that the hardened dental material will have a life-like luster. The dental materials of the present invention preferably have a visual opacity of about 0.05 to 0.4; more preferably about 0.05 to 0.35; most preferably about 0.05 to 0.25.

It has been found that materials of the invention, although filled at relatively high levels with nano-sized silica particles, still possess good rheological properties. These properties as well as strength can be enhanced by using surface-modifying agents to treat the surface of the particles. Surface treatment (surface-modification) enhances the dispersibility of the particles and their ability to bind into the matrix.

Practitioners generally desire good handling properties in a dental material, as it often translates to time savings. For example, in dental restorative work, it is desirable that dental materials do not slump because after a practitioner places the material in the mouth and manipulates the material by contouring and feathering, the practitioner generally wants the imparted shape to remain unchanged until the material is hardened. Materials used for restorative work, having a sufficiently high yield stress generally will not slump; that is, they will not flow under the stress of gravity. The yield stress of a material is the minimum stress required to cause the material to flow, and is described in "Rheology Principles, Measurements, and Applications" by C. W. Macosko, VCH Publishers, Inc., New York, 1994, p. 92. If the stress due to gravity is below the yield stress of the material, then the material will not flow. The stress due to gravity, however, will depend on the mass of dental material being placed as well as the shape.

"Contouring" refers to the process of shaping a material (using dental instruments) so that it resembles the natural dental anatomy. For easy contouring, materials should have a sufficiently high viscosity that they maintain their shape after manipulation with a dental instrument, and yet the viscosity should not be so high that it is difficult to shape the material. "Feathering" refers to the process of reducing the dental material to a thin film in order to blend the material into the natural dentition. This is done with a dental instrument at the margin of the manipulated material and the natural dentition. It is also desirable that the dental material not stick to placement instruments, to minimize further alteration of the shape or surface topography.

In a preferred embodiment where the dental material of the invention is a restorative, the dental material preferably has little to no slump, yet easily adapts to, for example, a cavity preparation, and is easily contoured and feathered. Preferably, the dental materials of the invention do not stick to placement instruments, and are advantageously, overall, fast and easy to use in dental procedures such as, for example, restoring tooth structure.

Surprisingly, it has been found that the dental materials of the invention can possess improved and desirable shear thinning behavior. That is, they can have a low viscosity when subjected to high stress, and high viscosity when subjected to low stress. The low viscosity under high stress allows a practitioner to feather the material over a tooth surface and carve the dental material. Advantageously, the high viscosity under low stress allows the material to maintain its shape (i.e. no slumping) after a practitioner manipulates the material to match the contour of the tooth.

The silica is dispersed within the hardenable resin matrix. The silica particles used in the dental materials of the invention preferably have an average diameter of less than about 200 nm; more preferably, the particles are less than about 100 nm in average diameter. These measurements are preferably based on a TEM (transmission electron microscopy) method, whereby a population of particles such as what is show in FIG. 1, is analyzed to obtain an average particle diameter. A preferred method for measuring the particle diameter is set out below, in the Test Methods section. In FIG. 1, preferred silica particles dispersed in a hardenable resin are shown. The average surface area of the silica particles is preferably greater than about 15 m$^2$/g; more preferably greater than about 30 m$^2$/g.

Once dispersed in the resin, the silica particles are in a discrete (individual) and unassociated (i.e. non-agglomerated, non-aggregated) condition. "Agglomerated"

as used herein, is descriptive of a weak association of particles usually held together by charge or polarity and can be broken down into smaller entities. "Aggregated," as used herein, is descriptive of a strong association of particles often bound together by, for example, residual chemicals treatment; further breakdown of the aggregates into smaller entities is very difficult to achieve.

The silica particles used in the dental materials of the present invention are preferably substantially spherical and substantially non-porous. Although the silica is preferably essentially pure, it may contain small amounts of stabilizing ion such as ammonium and alkaline metal ions.

Preferred nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329. In a preferred embodiment where the hardenable resin employs a cationic initiation system, the starting silica is preferably acidic (such as Nalco 1042).

Optionally, fumed silica can be included in the materials of the invention in addition to the nano-sized silica particles described above. Suitable fumed silicas include for example, products sold under the tradename AEROSIL series OX-50, -130, -150, and -200 available from DeGussa AG, (Hanau, Germany), and CAB-O-SIL M5 available from Cabot Corp (Tuscola, Ill.).

Surface-treating the nano-sized silica particles before loading into the dental material can provide a stable dispersion in the resin. "Stable", as used herein, means a dental material in which the particles do not agglomerate after standing for a period of time, such as about 24 hours, under standard ambient conditions—e.g. room temperature (about 20–22° C.), atmospheric pressure, and no extreme electromagnetic forces. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

The silica particles of the present invention are preferably treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Upon surface treating the silica particles, they can then be combined with an appropriate hardenable resin to form a dental material of the invention. The silica particles are preferably present in amounts greater than about 40 weight percent (wt. %) of the total weight of the dental material. More preferably, the silica particles are present in an amount of about 40 wt % to about 90 wt %; most preferably, the silica particles are present in an amount of about 50 wt % to about 75 wt %.

Optionally, a heavy metal oxide can be included in the dental materials of the invention to provide a radiopaque dental material. It is preferred that the heavy metal oxide be present in an amount effective to impart radiopacity. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides of heavy metals having an atomic number greater than about 28 are preferred. The heavy metal oxide should be chosen such that undesirable colors or shading are not imparted to the hardened resin in which it is dispersed. For example, iron and cobalt would not be favored, as they impart dark and contrasting colors to the neutral tooth color of the dental material. More preferably, the heavy metal oxide is an oxide of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof.

The heavy metal oxide components, as well as other additives, may be included in the dental materials of the invention in various forms, including for example, particles on the silica surface or amongst the silica particles, or a coating on at least a portion of the surface of a silica particle. Preferably, the heavy metal oxide component is provided as a sol or individual particles.

It has been found that incorporation of an effective amount of nano-sized heavy metal oxide particles into dental materials of the invention can yield optically translucent materials with high X-ray opacity and high refractive index. The heavy metal oxide particles preferably have an average diameter of less than about 100 nm. More preferably, the particles are less than about 70 nm, more preferably less than about 60 nm in average diameter. The heavy metal oxide particles may be aggregated. If so, it is preferred that the aggregated particles are less than about 200 nm, and more preferably are less than about 90 nm in average diameter.

Preferred sources of unassociated heavy metal oxide aprticles are sols having particles dispersed in a solution. A zirconia sol, as disclosed in U.S. Pat. No. 5,037,579 (Matchett), is a suitable and preferable heavy metal oxide for use with the dental materials of the invention.

Another preferred zirconia sol is disclosed by Kolb in U.S. Patent Application Ser. No. 09/428,374, entitled "Zirconia Sol and Method of Making Same" filed on even date with the present invention, and which is incorporated herein. Zirconia sols of Application Ser. No. 09/428,374 comprise a plurality of single crystal zirconia particles having an average primary particle size of about 20 nm or less, more preferably, having an average primary particle size ranging from about 7–20 nm. As used herein, the term "primary particle size" refers to the size of a non-associated single crystal zirconia particle. Primary particle size is determined by the test method entitled, Crystallite Particle Size and Crystal Form Content, a procedure which resides in the Test Methods section below.

As disclosed in Application Ser. No. 09/428,374 the zirconia sols comprise zirconia particles which are highly crystalline in nature. This is important in that crystalline zirconia has a higher refractive index and higher x-ray scattering capability than amorphous zirconia. Crystallinity of zirconia particles may be quantified, for example, using a crystallinity index. Crystallinity index is calculated by dividing the x-ray scattering intensity of the sample material by the x-ray scattering intensity of a known crystalline standard material, for example, calcium stabilized zirconium oxide. A specific test procedure for determining the crystallinity index of zirconia particles is entitled Crystallinity Index Procedure, a description of which resides in the Test Methods section below. In the zirconia sols, the zirconia particles have a crystallinity index of about 0.65 or greater. More preferably, the zirconia particles having a crystallinity index of about 0.75 or greater, most preferably about 0.85 or greater.

Of the crystalline portion of the zirconia particles, the predominate crystal lattice forms are cubic and tetragonal with a minor amount of monoclinic phase also being present. Due to the difficulty in separately quantifying cubic and tetragonal crystal lattice structures using x-ray diffraction, the two have been combined and are reported herein as combined cubic and tetragonal. Specifically, the zirconia particles comprise about 70% or greater combined cubic and tetragonal crystal lattice structure. More preferably, the zirconia particles comprise about 75% or greater combined cubic and tetragonal crystal lattice structure, and most preferably comprise about 85% or greater combined cubic and tetragonal crystal lattice structure. In each instance, the balance of the crystalline phase is in the monoclinic crystal lattice structure.

Due to their very small size, the zirconia particles exist in predominately cubic and tetragonal crystal lattice phases without need for an effective amount of a crystal phase stabilizer. As used herein the term "crystal phase stabilizer" refers to a material which may be added to stabilize zirconia in the cubic and/or tetragonal crystal lattice structure. Specifically, crystal phase stabilizers function to suppress transformation from the cubic and/or tetragonal phase to the monoclinic phase. Crystal phase stabilizers include, for example, alkaline-earth oxides such as MgO and CaO, rare earth oxides (i.e., lanthanides) and $Y_2O_3$. "An effective amount" refers to the amount of crystal phase stabilizer necessary to suppress transformation of zirconia from the cubic and/or tetragonal phase to the monoclinic phase. In a preferred embodiment, the zirconia particles comprise less than about 1 wt. % of a crystal phase stabilizer, more preferably less than about 0.1 wt. % of a crystal phase stabilizer.

In zirconia sols of Application Ser. No. 09/428,374, the primary particles of zirconia exist in a substantially non-associated (i.e., non-aggregated and non-agglomerated) form. A quantitative measure of the degree of association between the primary particles in the sol is the dispersion index. As used herein the "dispersion index" is defined as the hydrodynamic particle size divided by the primary particle size. The primary particle size is determined using x-ray diffraction techniques as described in the test procedure "rystallite Aprticle Size and Crystal Form Content" set out below. Hydrodynamic particle size refers to the weight average particle size of the zirconia particles in the aqueous phase as measured by Photon Correlation Spectroscopy (PCS), a description of which resides in the Test Mehtods section below. If the primary particles are associated, PCS provides a measure of the size of the aggregates and/or agglomerates of primary particles in the zirconia sol. If the particles are non-associated, PCS provides a measure of the size of the primary particles. Accordingly, as the association between primary particles in the sol decreases the dispersion index approaches a value of 1. In the zirconia sols, the primary zirconia particles exist in a substantially non-associated form resulting in a zirconia sol having a dispersion index ranging from about 1–3, more preferably ranging from about 1–2.5, and most preferably ranging from about 1–2.

As further taught in Application Ser. No. 09/428,374, suitable starting materials for preparing polyether acid zirconium salts include basic zirconium salts such as zirconium carboxylates and basic zirconium salts having counterions that may be displaced with carboxylic acids. Representative examples of basic zirconium salts having counterions that may be displaced with carboxylic acids include zirconium oxynitrate, zirconium oxychloride and zirconium carbonates. Basic zirconium salts are salts of zirconium wherein at least a portion of the cationic charge on the zirconium is compensated by hydroxide or an $O^{2-}$ anion. Because it is difficult in practice to determine whether the oxygen content in basic zirconium salts arises from bound hydroxide or $O^{2-}$, it is common to represent this oxygen content as simply oxygen. Thus, formula (1) set forth below is presented with bound water excluded for simplicity and represents a general formula for zirconium compounds that may be suitable as starting materials for preparing polyether acid zirconium salts.

$$ZrO_{(4-n/2)}(X)_n \qquad (1)$$

where: X is a carboxylic acid displaceable counterion; and n ranges from 0.5 to 4.

Representative examples of carboxylic acid displaceable counterions include carboxylates such as acetates, formates and propionates and other counterions such as nitrate, chloride, carbonate or a combination thereof. Zirconium alkoxides, although not formally zirconium salts, may be used as starting materials in the formation of the polyether acid zirconium after initial reaction with a suitable acid to form a basic zirconium salt.

A preferred starting material is an aqueous solution or sol of basic zirconium acetate having the general formula $ZrO_{(4-n/2)}(CH_3COO)_n$, where n ranges from about 1–2. In aqueous solutions, zirconium acetate probably exists as complex polynuclear zirconium cation. Processes for making zirconium acetate are well known in the art (see, for example, W. B. Blumenthal, "The Chemical Behavior of Zirconium", D. Van Nostrand Company, Princeton, N.J., pp. 311–338). Suitable zirconium acetate solutions comprise from about 5–40 wt. % as $ZrO_2$ and range from about 5–40 wt. % acetate. A preferred zirconium acetate sol starting material comprises $ZrO_{1.25}(C_2H_3O_2)_{1.5}$ at 20 wt. % $ZrO_2$ and is commercially available under the trade designation "Nyacol $ZrO_2(Ac)$" from Nyacol Products Corp., Ashland, Mass.

In a preferred process of Application Ser. No. 09/428,374 a polyether acid zirconium salt is prepared by reacting, in an aqueous solution, a zirconium salt with a polyether carboxylic acid. As presently understood, the polyether carboxylic acid is believed to function to prevent association (i.e., agglomeration and/or aggregation) of the zirconia particles as they are formed during the hydrolysis reaction. In this way, the zirconia particles produced according to the process are substantially non-associated.

Polyether carboxylic acids suitable for use as modifiers in Application Ser. No. 09/428,374 are water soluble monocarboxylic acids (i.e., containing one carboxylic acid group per molecule) having a polyether tail. The polyether tail comprises repeating difunctional alkoxy radicals having the general formula —O—R—. Preferred R groups have the general formula —$C_nH_{2n}$— and include, for example, methylene, ethylene and propylene (including n-propylene and i-propylene) or a combination thereof. Combinations of R groups may be provided, for example, as random, or block type copolymers.

A preferred class of monovalent polyether radicals may be represented generally by formula (3):

$$CH_3\text{—}[O\text{—}(CH_2)_y]_x\text{—}X\text{—}COOH \quad (3)$$

where:

X is a divalent organic linking group;

x ranges from about 1–10; and y ranges from about 1–4.

Representative examples of X include —$X_2$—$(CH_2)_n$— where $X_2$ is —O—S—, —C(O)O—, —C(O)NH— and wherein n ranges from about 1–3.

Examples of preferred polyether carboxylic acids include 2-[2-(2-methoxyethoxy)ethoxy] acetic acid having the chemical structure $CH_3O(CH_2CH_2O)_2CH_2COOH$ (hereafter MEEAA) and 2-(2-methoxyethoxy) acetic acid having the chemical structure $CH_3OCH_2CH_2OCH_2COOH$ (hereafter MEAA). MEAA and MEEAA are commercially from Aldrich Chemical Co., Milwaukee, Wis. as catalog numbers 40,701-1 and 40,700-3, respectively. It is also within the scope of this invention to utilize a mixture of more than one polyether carboxylic acid.

Reaction of the polyether carboxylic acid with a zirconium salt following reaction sequence (1):

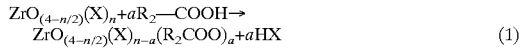

$$ZrO_{(4-n/2)}(X)_n + aR_2\text{—}COOH \rightarrow$$
$$ZrO_{(4-n/2)}(X)_{n-a}(R_2COO)_a + aHX \quad (1)$$

results in the formation of a polyether acid zirconium salt having the general formula $ZrO_{(4-n/2)}(X)_{n-a}(R_2COO)_a$ and liberates (i.e., releases) approximately a stoichiometric amount of an acid having the general formula HX. By way of example, when the zirconium salt comprises zirconium acetate $(ZrO_{(4-n/2)}(C_2H_3O_2)_n)$ a near stochiometric amount of acetic acid $(C_2H_3O_2H)$ is released as a result of the formation of the polyether acid zirconium salt (see, reaction sequence 1a).

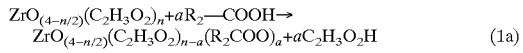

$$ZrO_{(4-n/2)}(C_2H_3O_2)_n + aR_2\text{—}COOH \rightarrow$$
$$ZrO_{(4-n/2)}(C_2H_3O_2)_{n-a}(R_2COO)_a + aC_2H_3O_2H \quad (1a)$$

Salts of zirconium with carboxylic acids are not dissociated in the aqueous phase as the acid is bound to the zirconium atom. The carboxylic acid effects the water solubility of the salt. Attachment of hydrophobic acids (e.g., alkyl acids) to the zirconium causes the salts to be insoluble in water. In fact, even the addition of small acids such as propionic acid and acrylic acid cause the salt to be insoluble in water. In contrast, the polyether acids used in Application Ser. No. 09/428,374 allow higher molecular weight acids to be used while maintaining the water solubility of the polyether acid zirconium salt. This in turn allows hydrothermal treatment of the dissolved polyether acid zirconium salt in the aqueous phase.

Typically, relative to the zirconium salt starting material, the polyether carboxylic acid is added in an amount ranging from about 2.5–5.0 millimoles per gram equivalent of $ZrO_2$ in the zirconium salt. For the preferred zirconium acetate starting material (i.e., Nyacol $ZrO_2(Ac)$), this range results in the displacement of about 20–50% of the acetate groups. Preferably, the amount of polyether carboxylic acid added should be limited to the minimum amount necessary to prevent association of the resulting zirconia particles. In this way, the amount of acid released during formation of the polyether acid zirconium salt is kept to a minimum. The amount of polyether carboxylic acid added may depend upon such factors as, for example, the molecular weight of the polyether carboxylic acid, the concentration, time and temperature during the hydrolysis reaction.

In further teachings of application No. 5520QUSA5A, typically, the polyether carboxylic acid is added to an aqueous solution of the zirconium salt and the resulting solution is stirred at room temperature for about 30–60 minutes. The polyether carboxylic acid molecules react with the zirconium salt displacing and substituting for at least a portion of the acid groups bound to the zirconium salt. The displaced acid groups are released into the solution as free acid. It will ordinarily be preferred to remove at least a portion of the acid, more preferably substantially all of the acid released during the formation of the polyether acid zirconium salt. It should be noted that removal of the acid may function to shift the reaction equilibrium towards formation of the polyether acid zirconium salt. Suitable techniques for removing the excess acid are known in the art and include, for example, drying or distillation. When the liberated acid has a low boiling point (e.g., < about 175° C.), it may be removed by heating the solution until the aqueous phase evaporates leaving a residue of the polyether acid zirconium salt. The polyether acid zirconium salt must then be dissolved in water prior to hydrolysis.

After formation of the polyether acid zirconium salt and, preferably, removal of the liberated acid, the next step is to hydrolyze an aqueous solution of the polyether acid zirconium salt under conditions sufficient to convert the polyether acid zirconium salt into crystalline zirconia particles. By way of example, when the polyether acid zirconium salt is derived from the acetate salt (see, reaction sequence 1a), the hydrolysis step follows general reaction sequence (2a):

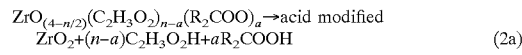

$$ZrO_{(4-n/2)}(C_2H_3O_2)_{n-a}(R_2COO)_a \rightarrow \text{acid modified}$$
$$ZrO_2 + (n-a)C_2H_3O_2H + aR_2COOH \quad (2a)$$

The hydrolysis reaction forms acid modified zirconia particles and also produces free carboxylic acids (i.e., $C_2H_3O_2H$ and $R_2COOH$) as a by product. Therefore, the resultant zirconia sol comprises the acid modified zirconia particles and a mixture of two carboxylic acids in water. By acid modified zirconia particles it is meant that at least a fraction of the acids are adsorbed to the surface of the zirconia particles.

The hydrolysis reaction of the polyether acid zirconium salt solution may take place in any suitable reaction vessel. Since the reaction is typically performed under high temperatures and pressures, an autoclave will generally be the preferred type of reaction vessel. One example of a preferred reaction vessel is commercially available as Pressure Reactor Series #4520"from Parr Instruments Co., Moline, Ill.

In operation of the process of Application Ser. No. 09/428,374, an aqueous solution of the polyether acid zirconium salt is first charged into a reaction vessel. The concentration of the polyether acid zirconium salt solution is typically in the range of 0.5–3 wt. % $ZrO_2$, preferably in the range of 1–2 wt. % $ZrO_2$. However, the concentration may be varied through a wider range depending upon the other reaction conditions. The polyether acid zirconium salt solution is then heated to a temperature sufficient to convert it into zirconia particles. Preferred hydrolysis temperatures range from about 140–250° C., more preferably ranging from about 150–200° C. Typically the reaction vessel is heated to the desired hydrolysis temperature over a period of several hours. Among other considerations, a suitable hydrolysis temperature or temperature range, may be selected in order to minimize degradation and/or decomposition of the polyether carboxylic acid. The pressure maintained in the reaction vessel may be the autogenous pressure (i.e., the vapor pressure of water at the temperature of the reaction) or, preferably, the reaction vessel may be pressured, for example, with an inert gas such as nitrogen. Preferred pressures range from about 1–30 bars. Pressurization of the reaction vessel is believed to reduce or eliminate refluxing of the polyether acid zirconium salt solution within the reaction vessel which may deleteriously affect the properties of the resulting zirconia sol. The time of hydrolysis is typically a function of the hydrolysis temperature and the concentration of the salt solution. Heat is typically applied until the hydrolysis reaction is substantially complete. Generally, the time involved is in the range of about 16–24 hours at a temperature of about 175° C., however, longer or shorter times may also be suitable. The reaction may be monitored by examining the resulting zirconia particles using x-ray diffraction or by examining the amount of free acid in the water phase using IR spectroscopy or HPLC. Upon completion of the hydrolysis, the pressure vessel is allowed to cool and the resulting zirconia sol is removed from the reaction vessel. Although the procedure described above is a batchwise process, it is also within the scope of this invention to conduct the hydrolysis in a continuous process.

Zirconia sols of Application Ser. No. 09/428,374 may be concentrated by removing at least a portion of the liquid phase using techniques well known in the art, for example, evaporation or ultra-filtration. In a preferred method the zirconia sols are concentrated to about 10–40 wt. % $ZrO_2$ using a rotary evaporator.

Zirconia sols prepared in accordance with the method of Application Ser. No. 09/428,374 typically contain an excess of acid over that normally desired (see, reaction sequence 2a). When it is desired to combine a zirconia sol with an organic matrix material, for example, an organic monomer, it will ordinarily be necessary to remove at least a portion of, more preferably substantially all of, the free acid present in the sol. Typically, the acid may be removed by such conventional methods as drying, dialysis, precipitation, ion exchange, distillation or diafiltration.

Due to the formation of free acid during the hydrolysis reaction, the pH of the as prepared zirconia sols typically ranges from about 1.8–2.2. Dialysis may be used to increase the pH of the sols. Dialyzed sols typically have a pH ranging about 1–4.5, or greater, depending upon the extent of the dialysis. The pH of the sols may also be adjusted by the addition of acids (e.g., concentrated HCl and glacial acetic) and/or base (e.g., aqueous ammonia). Addition of aqueous ammonia has resulted in clear sol to at least pH 6–7.

Dialysis, ion exchange and diafiltration methods may be used to remove the free acid without substantially changing the ratio of the acids adsorbed to the surface of the zirconia particles. Alternatively, removal of excess acid and concentration of the sol may be achieved by first evaporating the water and free acid from the sol to obtain a dry powder. The dry powder may then be redispersed in a desired amount of water to obtain a concentrated sol substantially free of excess acid. It should be noted, however, that this technique may change the ratio of the acids adsorbed to the surface of the zirconia particles in such a way that the ratio of the higher boiling acid to the lower boiling acid is increased.

Optionally, after formation of the zirconia sol, the polyether carboxylic acid groups may be removed or displaced from the zirconia particles of the sol. Removal of the polyether carboxylic acid groups may be advantageous, for example, when the polyether groups would be incompatible with an organic matrix material to which it is desired to add the zirconium sol. Displacement of the polyether carboxylic acid groups may be accomplished, for example, by displacing the polyether acid from the zirconia particles with a carboxylic acid, for example, acetic acid. The carboxylic acid displaces and substitutes for the polyether carboxylic acid groups on the zirconia particles. After displacement, the free polyether carboxylic acid may be removed from the sol using techniques known in the art, for example, dialysis or diafiltration.

Surface treatment of the heavy metal oxide particle promotes the provision of stabilized nano-sized heavy metal oxide particles. Stabilization allows the heavy metal oxide particles to be well dispersed within the hardenable resin, so as to provide the desired translucency and yet provide the desired mechanical properties (e.g. strength) and radiopacity. A surface treatment agent is preferably chosen to contain functional groups that provide dispersibility and/or reactivity of the surface modified heavy metal oxide particle with(in) the desired hardenable resin. Preferably, the metal oxide particles are treated with an acidic compound. Suitable surface-treatment acids include for example, carboxylic acids, phosphonic acids, and sulfonic acids. More preferably, the surface stabilization is performed with a mixture of acidic compounds. Alternatively, a mixture of acidic compounds where one or more has a polymerizable functionality, can preferably be used. Most preferably, the acidic function is derived from oxyacids of boron, carbon, phosphorus, and sulfur. For example, it has been found that carboxylic acids adsorb particularly well to the surface of zirconia and ceria particles.

A mixture of acids is preferably used to surface treat (modify) the heavy metal oxide particles. Preferably, the acids include the structure R—COOH, where R is an organic radical containing ethylenic unsaturation. R may be branched or straight chained and may be substituted (e.g., by a heteroatom). R typically contains from about 1 to 50 carbon atoms, preferably about 2 to 20 carbon atoms. A particularly preferred group of such acids includes R groups with terminal ethylenic unsaturation.

Adsorption of a combination of acids to the particle surface provides a desirable surface modification to impart strength, dispersibility and stability. In a preferred method, zirconia particles are dispersed in water with acetic acid adsorbed to the surface. The surface modification involves replacement of adsorbed acetic acid with a combination of acids chosen to provide good dispersion and high strength to the final material.

Hydrophilic, non-reactive acids suitable for the surface treatment (modification) include 2-[2-(2-methoxy)ethoxy] ethoxy acetic acid (MEEAA), mono(polyethyleneglycol) succinate, mono(polyethyleneglycol)maleate. These acids provide good dispersion of the particles in the hardenable dental materials of the invention.

Strength is greatly enhanced via copolymerization of surface modifying groups with the hardenable resin. Preferably, this is accomplished by using a reactive surface modifier. Examples of hydrophilic and reactive acids suitable for the surface treament include 2-hydroxymethyl-2-[(N-methacryloxyethyl)carbamoylmethyl]propionic acid (PAMA), mono(acryloxypolyethyleneglycol)succinate, and mono(acryloxypolyethyleneglycol)maleate. Other suitable reactive acids include 2,2-bis[(N-methacryloxyethyl) carbamoylmethyl]propionic Acid (PDMA), acrylic acid, methacrylic acid, beta carboxyethylacrylate, mono-2-(methacryloxy)ethyl succinate, and mono-2-(methacryloxy) ethyl maleate.

Combinations of such acids are also desirable to impart organic compatibility and reactivity. Other suitable acid mixtures useful for surface treatment of the heavy metal oxide can include aliphatic carboxylic acids such as, for example, oleic acid, stearic acid, and octanoic acid, aromatic nonreactive acids such as methoxy phenyl acetic acid and 3,4,5 triethoxy benzoic acid, as well as itaconic acid, toluene sulfonic acid, ethylene glycol methacrylate phosphate, the salts of the acids just stated, and blends thereof.

The dental materials of the present invention include a hardenable resin. These resins preferably are generally thermosetting resins capable of being hardened to form a polymer network such as, for example, acrylate resins, methacrylate resins, epoxy resins, vinyl resins or mixtures thereof. Preferably, the hardenable resin is made from one or more matrix-forming oligomer, monomer, or polymer, or blend thereof.

In a preferred embodiment where the dental material of the invention is a dental composite, polymerizable resins suitable for use include hardenable organic resins having sufficient strength, hydrolytic stability, and non-toxicity to render them suitable for use in the oral environment. Examples of such resins include acrylate, methacrylate, urethane, carbamoylisocyanurate and epoxy resins, e.g., those shown in U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,308,190, 4,327,014, 4,379,695, 4,387,240 and 4,404,150, and mixtures and derivatives thereof.

One class of preferred hardenable resins are materials having free radically active functional groups and include monomers, oligomers, and polymers having one or more ethylenically unsaturated groups. Alternatively, the hardenable resin can be a material from the class of resins that include cationically active functional groups. In another alternative, a mixture of hardenable resins that include both cationically curable and free radically curable resins may be used for the dental materials of the invention.

In the class of hardenable resins having free radically active functional groups, suitable materials for use in the invention contain at least one ethylenically unsaturated bond, and are capable of undergoing addition polymerization. Such free radically polymerizable materials include mono-, di- or poly-acrylates and methacrylates such as methyl acrylate. methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically an be capable of generating free radicals for addition polymerization upon exposure to light energy having a wavelength between 200 and 800 nm.

A variety of visible or near-IR photoinitiator systems may be used for photopolymerization of free-radically polymerizable materials useful in the invention. For example, in free radical polymerization (hardening), a photoinitiation system can be selected from systems which initiate polymerization via a two component system of an amine and an α-diketone as described in U.S. Pat. No. 4,071,424, which is herein incorporated by reference. Alternatively, the resin can be combined with a three component or ternary photoinitiator system such as described in U.S. Pat. No. 5,545,676 which is incorporated herein by reference.

In the ternary photoinitiator system, the first component is an iodonium salt, i.e., a diaryliodonium salt. The iodonium salt is preferably soluble in the monomer and shelf-stable (i e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt (e.g., containing an anion such as Cl$^-$, Br$^-$, I$^-$ or $C_4H_5SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula:

ACO(X)$_b$B where X is CO or CR$^5$R$^6$, where R$^5$ and R$^6$ can be the same or different, and can be hydrogen, alkyl, alkaryl or aralkyl, b is zero or one, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxybenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incoporated herein by reference.

Alternatively, free-radical initiators useful in the invention include the class of acylphosphine oxides, as described in European Patent Application No. 173567, U.S. Pat. No. 4,737,593 and United Kingdom Pat No. GB 2,310,855. Such acylphosphine oxides are of the general formula

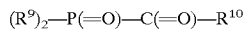
(R$^9$)$_2$—P(=O)—C(=O)—R$^{10}$ wherein each R$^9$ individually can be a hydrocarbyl group such as alkyl, cycloalkyl, aryl, and aralkyl, any of which can be substituted with a halo-, alkyl- or alkoxy-group, or the two R$^9$ groups can be joined to form a ring along with the phosphorous atom, and wherein R$^{10}$ is a hydrocarbyl group, an S—, O—, or N— containing five- or six-membered heterocyclic group, or a —Z—C(=O)—P(=O)—(R$^9$)$_2$ group, wherein Z represents a divalent hydrocarbyl group such as alkylene or phenylene having from 2 to 6 carbon atoms.

Preferred acylphosphine oxides useful in the invention are those in which the R$^9$ and R$^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. The initiator can be employed in catalytically-effective amounts, such as from about 0.1 to about 5 weight percent, based on the weight of ethylenically-unsaturated compound present, of the acylphosphine oxide plus from about 0.1 to about 5 weight percent, based on the weight of ethylenically-unsaturated compound present, of the tertiary amine.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis(η$^5$-2,4-cyclopentadien-1-yl)-bis (2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the dental materials of the invention includes the class of ionic dye—counterion complex initiators comprising a borate anion and a complementary cationic dye.

Borate salt photoinitiators are described, for example, in U.S. Pat. Nos. 4,772,530, 4,954,414, 4,874,450, 5,055,372, and 5,057,393, the disclosures of which are incorporated herein by reference.

Borate anions useful in these photointiators generally can be of the formula

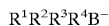

wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium. Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. to 15° C. under normal conditions or at elevated pressure. This procedure is preferred for initiating polymerization of materials occurring outside of the oral environment.

Yet another alternative class of initiators capable of initiating polymerization of free radically active functional groups that are useful for the dental materials of the invention are those that include free radical-generating thermal initiators. Examples include peroxides such as, for example, benzoyl peroxide and lauryl peroxide, and azo compounds such as, for example, 2,2-azobis-isobutyronitrile (AIBN).

An alternative class of hardenable resins useful in the dental materials of the invention may include cationically active functional groups. Materials having cationically active functional groups cationically polymerizable epoxy resins, vinyl ethers, oxetanes, spiro-orthocarbonates, spiro-orthoesters, and the like.

Preferred materials having cationically active functional groups are epoxy resins. Such materials are organic compounds having an oxirane ring, i.e., a group of the formula

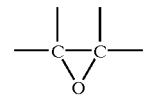

which is polymerizable by ring opening. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexane oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, which is incorporated herein by reference.

Further epoxy-containing materials which are useful in the compositions of this invention include glycidyl ether monomers of the formula

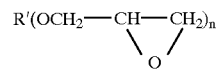

where R' is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type are described in U.S. Pat. No. 3,018,262, which is incorporated herein by reference, and in "Handbook of Epoxy Resins" by Lee and Neville, McGraw-Hill Book Co., New York (1967).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, alkylene oxides, e.g., propylene oxide, styrene oxide; alkenyl oxides, e.g., butadiene oxide; glycidyl esters, e.g., ethyl glycidate.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar.

There are a host of commercially available epoxy resins which can be used in this invention. In particular, epoxides which are readily available include octadecylene oxide, epichlorohydrin, styrene oxide, vinylcyclohexene oxide, glycidol, glycidyl methacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "CYRACURE UVR 6110" or "UVR 6105" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN431" and "DEN438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy) cyclohexane-meta-dioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., HELOXY Modifier 61" from Shell Chemical Co.), cresyl glycidyl ether (e.g., "HELOXY Modifier 62" from Shell Chemical Co.), p-ter butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2, 3-epoxypropoxy)-phenyl]fluorenone (e.g., "Epon 1079" from Shell Chemical Co.).

It is also within the scope of this invention to use one or more epoxy resins blended together. The different kinds of resins can be present in any proportion.

Optionally, monohydroxy- and polyhydroxy-alcohols may be added to the curable compositions of the invention, as chain-extenders for the epoxy resin. The hydroxyl-containing material used in the present invention can be any organic material having hydroxyl functionality of at least 1, and preferably at least 2.

Preferably the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e., from about 32 to 200, intermediate molecular weight, ie., from about 200 to 10,000, or high molecular weight, i.e., above about 10,000. As used herein, all molecular weights are weight average molecular weights.

The hydroxyl-containing material can optionally contain other functionalities that do not substantially interfere with cationic cure at room temperature. Thus, the hydroxyl-containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic cure at room temperature. The hydroxyl-containing material can, for example, be selected from naturally occurring or synthetically prepared cellulosic materials. Of course, the hydroxyl-containing material is also substantially free of groups which may be thermally or photolytically unstable; that is, the material will not decompose or liberate volatile components at temperatures below about 100° C. or in the presence of actinic light which may be encountered during the desired curing conditions for the photocopolymerizable composition. Useful hydroxyl-containing materials are described, for example, in U.S. Pat. No. 5,856,373, which is incorporated herein by reference.

The amount of hydroxyl-containing organic material used in the compositions of the invention may vary over broad ranges, depending upon factors such as the compatibility of the hydroxyl-containing material with the epoxide, the equivalent weight and functionality of the hydroxyl-containing material, the physical properties desired in the final cured composition, the desired speed of photocure, and the like.

Blends of various hydroxyl-containing materials may be useful in the dental materials of the invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

For hardening resins comprising cationically active functional groups, an initiation system can be selected from systems which initiate polymerization via radiation, heat, or redox/auto-cure chemical reaction. For example, epoxy polymerization may be accomplished by the use of thermal curing agents, such as anhydrides or amines. A particularly useful example of an anhydride curing agent would be cis-1,2-cyclohexanedicarboxylic anhydride.

Alternatively and preferably, initiation systems for resins comprising cationically active functional groups are those that are photoactivated. The broad class of cationic photoactive groups recognized in the catalyst and photoinitiator industries may be used in the practice of the present invention. Photoactive cationic nuclei, photoactive cationic moieties, and photoactive cationic organic compounds are art recognized classes of materials as exemplified by U.S. Pat. Nos. 4,250,311; 3,708,296; 4,069,055; 4,216,288; 5,084,586; 5,124,417; 4,985,340, 5,089,536, and 5,856,373, each of which is incorporated herein by reference.

The cationically-curable materials can be combined with a three component or ternary photoinitiator system, as described above. Three component initiator systems are also described in U.S. patent application Ser. Nos. 08/838,835, and 08/840,093, both of which are now allowed, each of which is incorporated herein by reference.

For hardening cationically curable resins, examples of useful aromatic iodonium complex salts (i.e. the first component of the ternary photoinitiator system) include: diphenyliodonium tetrafluoroborate; di(4-methylphenyl) iodonium tetrafluoroborate; phenyl-4-methylphenyliodonium tetrafluoroborate; di(4-heptylphenyl)iodonium tetrafluoroborate; di(3-nitrophenyl) iodonium hexafluorophosphate; di(4-chlorophenyl) iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl) iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate (DPISbF$_6$).

Of the aromatic iodonium complex salts which are suitable for use in the compositions of the invention diaryliodoniun hexafluorophosphate and diaryliodonium hexafluoroantimonate are among the preferred salts. These salts are preferred because, in general, they promote faster reaction, and are more soluble in inert organic solvents than are other aromatic iodonium salts of complex ions.

As mentioned above, the second and third components of the ternary photoinitiator system are a sensitizer and an electron donor, respectively. The sensitizers useful in cationic polymerization of the dental materials of the invention are those that are described above for the free-radically cured materials. Similarly, the electron donors useful for cationic polymerization of the materials of the invention include those that are described above for the free-radically cured materials. However, in the case of cationically cured materials, the electron donor preferably meets the requirements set forth in U.S. application Ser. Nos. 08/838,835, and 08/840,093, both of which are now allowed, each of which is incorporated heron by reference, and are soluble in the polymerizable composition. The donor can also be selected in consideration of other factors, such as shelf stability and the nature of the polymerizable materials, iodonium salt and sensitizer chosen. A class of donor compounds that may be useful in the inventive systems may be selected from some of the donors described in U.S. Pat. No. 5,545,676.

The donor is typically an alkyl aromatic polyether or an N-alkyl arylamino compound wherein the aryl group is substituted by one or more electron withdrawing groups. Examples of suitable electron withdrawing groups include carboxylic acid, carboxylic acid ester, ketone, aldehyde, sulfonic acid, sulfonate and nitrile groups.

A preferred group of N-alkyl arylamino donor compounds is described by the following structural formula:

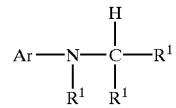

wherein each $R^1$ is independently H, $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, COOH, COOC$_{1-18}$ alkyl, $(C_{1-18}$ alkyl)$_{0-1}$—CO—$C_{1-18}$ alkyl, SO$_3$R$^2$, CN or an aryl group that is optionally substituted by one or more electron withdrawing groups, or the $R^1$ groups may bejoined to form a ring; and Ar is aryl that is substituted by one or more electron withdrawing groups. Suitable elctron withdrawing groups include —COOH, —COOR2, —SO$_3$R$^2$, —CN, —CO—C$_{1-18}$ alkyl and —C(O)H groups, wherein $R^2$ can be a $C_{1-18}$ straight-chain, branched, or cyclic alkyl group.

A preferred group of aryl alkyl polyethers has the following structural formula:

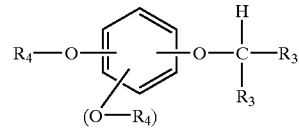

wherein n=1–3 each $R^3$ is independently H or $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —COOC$_{1-18}$ alkyl, —(C$_{1-18}$ alkyl)$_{0-1}$-COH, —(C$_{1-18}$ alkyl)$_{0-1}$-CO—C$_{1-18}$ alkyl, —CO—C$_{1-18}$ alkyl, —C(O)H or —C$_{2-18}$ alkenyl groups and each $R^4$ can be $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —COOC$_{1-18}$ alkyl, —(C$_{1-18}$ alkyl)$_{0-1}$-COH, —(C$_{1-18}$ alkyl)$_{0-1}$-CO—C$_{1-18}$ alkyl, —CO—C$_{1-18}$ alkyl, —C(O)H or —C$_{2-18}$ alkenyl groups.

In each of the above formulas the alkyl groups can be straight-chain or branched, and the cycloalkyl group preferably has 3 to 6 ring carbon atoms but may have additional alkyl substitution up to the specified number of carbon atoms. The aryl groups may be carbocyclic or heterocyclic aryl, but are preferably carbocyclic and more preferably phenyl rings.

Preferred donor compounds include 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile and 1,2,4-trimethoxybenzene.

An alternative photoinitiator system for cationic polymerizations includes the use of organometallic complex cations essentially free of metal hydride or metal alkyl functionality selected from those described in U.S. Pat. No. 4,985,340, and such description is incorporated herein by reference and has the formula:

$$[(L^1)(L^2)M]^{+q}$$

wherein

M represents a metal selected from the group consisting of Cr, Mo, W, Mn, Re, Fe, Ru, Os, Co, Rh, Ir, Pd, Pt and Ni, preferably Cr, Mo, W, Mn, Fe, Ru, Co, Pd, and Ni; and most preferably Mn and Fe;

$L^1$ represents 1 or 2 cyclic, polyunsaturated ligands that can be the same or different ligand selected from the group consisting of substituted and unsubstituted cyclopentadienyl, cyclohexadienyl, and cycloheptatrienyl, cycloheptatriene, cyclooctatetraene, heterocyclic compounds and aromatic compounds selected from substituted or unsubstituted arene compounds and compounds having 2 to 4 fused rinand units of polymers, e.g., a phenyl group of polystyrene, poly(styrene-co-butadiene), poly(styrene-co-methyl methacrylate), poly(a-methylstyrene), and the like; a cyclopentadiene group of poly(vinylcyclopentadiene); a pyridine group of poly(vinylpyridine), and the like, each capable of contributing 3 to 8 electrons to the valence shell of M;

$L^2$ represents none, or 1 to 3 nonanionic ligands contributing an even number of electrons that can be the same or different ligand selected from the group of carbon monoxide, ketones, olefins, ethers, nitrosonium, phosphines, phosphites, and related derivatives of arsenic and antimony, organonitriles, amines, alkynes, isonitriles, dinitrogen, with the proviso that the total electronic charge contributed to M results in a net residual positive charge of q to the complex;

q is an integer having a value of 1 or 2, the residual charge of the complex cation.

Organometallic salts are known in the art and can be prepared as described in, for example, EPO No. 094,914 and U.S. Pat. Nos. 5,089,536, 4,868,288, and 5,073,476, and such descriptions are incorporated herein by reference.

Examples of preferred cations include:

diphenyliodonium, ditolyliodonium, didodecylphenyliodonium, (4-octyloxyphenyl)phenyliodonium, and bis(methoxyphenyl)iodonium;

triphenylsulfonium, diphenyl-4-thiophenoxyphenylsulfonium, and 1,4-phenylene-bis(diphenylsufonium);

bis($\eta^5$-cyclopentadienyl)iron(1+), bis($\eta^5$-methylcyclopentadienyl)iron (1+), ($\eta^5$-cyclopentadienyl)($\eta^5$-methylcyclopentadienyl)iron (1+), and bis($\eta^5$-trimethylsilylcyclopentadienyl)iron (1+);

bis($\eta^6$-xylenes)iron (2+), bis($\eta^6$-mesitylene)iron (2+), bis($\eta^6$-durene)iron (2+), bis($\eta^6$-pentamethylbenzene)iron (2+), and bis($\eta^6$-dodecylbenzene)iron (2+);

($\eta^5$-cyclopentadienyl)($\eta^6$-xylenes)iron(1+), commonly abbreviated as (CpFeXy)(1+), ($\eta^5$-cyclopentadienyl)($\eta^6$-toluene)iron(1+),
($\eta^5$-cyclopentadienyl)($\eta^6$-mesitylene)iron(1+),
($\eta^5$-cyclopentadienyl)($\eta^6$-pyrene)iron(1+),
($\eta^5$-cyclopentadienyl)($\eta^6$-naphthalene)iron(1+), and
($\eta^5$-cyclopentadienyl)($\eta^6$-dodecylphenyl)iron(1+).

Alternatively, hardenable resins useful for the invention may have both cationically active and free radically active functional groups contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the "Cyclomer" series, such as Cyclomer M-100, M-101, or A-200 available from Daicel Chemical, Japan, and Ebecryl-3605 available from Radcure Specialties.

The photoinitiator compounds are preferably provided in the dental materials of the invention in an amount effective to initiate or enhance the rate of cure or hardening of the resin system. Photopolymerizable compositions useful in the invention are prepared by simply admixing, under "safe light" conditions, the components as described above. Suitable inert solvents may be employed if desired when effecting this mixture. Any solvent may be used which does not react appreciably with the components of the inventive compositions. Examples of suitable solvents include acetone, dichloromethane, and acetonitrile. A liquid material to be polymerized may be used as a solvent for another liquid or solid material to be polymerized. Solventless compositions can be prepared by simply dissolving an aromatic iodonium complex salt and sensitizer in an epoxy resin or epoxy resin-polyol mixture with or without the use of mild heating to facilitate dissolution.

Various methods can be employed to combine the sol (particles) and the hardenable resin. The objectives in the preparation are to facilitate the surface modification of the particles and to remove the water, excess solvent and/or salt by-products.

Generally, the process of making the dental materials of the invention involves surface modification of the particles followed by incorporation of the particles into the hardenable resin. The surface modification process involves the mixture of an inorganic sol with surface modifying agents. Optionally, a co-solvent can be added at this point, such as for example, methoxy propanol. The co-solvent can enhance the solubility of the surface modifying agents as well as the surface modified particles. The mixture comprising the inorganic sol and surface modifying agents is subsequently reacted at room or an elevated temperature, with or without mixing. In a preferred method, the mixture can be reacted at about 85° C. for about 24 hours, resulting in the surface modified sol. In a preferred method, where heavy metal oxides are included in the material of the composition, the surface treatment of the optional heavy metal oxide can preferably involve the adsorption of acidic molecules to the particle surface. The surface modification of the heavy metal oxide preferably takes place at room temperature.

The surface modified particles of silica alone or in combination with the heavy metal oxide can then be incorporated into the hardenable resin in various methods. In one aspect, a solvent exchange procedure is utilized whereby the hardenable resin is added to the surface modified sol, followed by removal of the water and co-solvent (if used) via evaporation, thus leaving the particles dispersed in the hardenable resin. The evaporation step can be accomplished for example, via distillation, rotary evaporation or oven drying.

In another aspect, the surface modified particles can be extracted into a water immiscible solvent followed by solvent exchange, if so desired.

Alternatively, another method for incorporating the silica and the hardenable resin involves the drying of the modified particles into a powder, followed by the addition of the resin material into which the particles are dispersed. The drying step in this method can be accomplished by conventional means suitable for the system, such as, for example, oven drying or spray drying. Where a spray drying technique is utilized, the inlet temperature is preferably at about 200° C. and the outlet temperature is preferably between about 85° C. to 100° C. In another aspect, conventional oven drying can be performed at between about 70° C. to 90° C. for about 2 to 4 hours.

Alternatively, in yet another aspect, the surface modified particles can be filtered to obtain solids which can be dried into a powder. This method is preferred when the particles of the surface modified aqueous sol have agglomerated due to the incompatibility of the surface treatment with the aqueous medium. The hardenable resin is then added to the dry, filtered particles to obtain the dental materials of the invention.

The dental materials of the present invention may optionally comprise additional adjuvants suitable for use in the oral environment, including colorants, flavorants, antimicrobials, fragrance, stabilizers, viscosity modifiers and fluoride releasing materials. For example, a fluoride releasing glass may be added to the materials of the inventiont to provide the benefit of long-term release of fluoride in use, for example in the oral cavity. Fluoroaluminosilicate glasses are particularly preferred. Particularly preferred are silanol treated fluoroaluminosilicate glass fillers, as described in U.S. Pat. No. 5,332,429, the disclosure of which is expressly incorporated by reference herein. Other suitable adjuvants include agents that impart fluorescence and/or opalescence.

In a preferred method of using the dental material of the invention, comprising a hardenable resin and fillers of the invention, the material is placed near or on a tooth surface, followed by a manipulation by the practitioner or laboratory to change the topography of the material, then hardening the resin. These steps can be followed sequentially or in a different order. For example, in a preferred embodiment where the dental material is a mill blank or a prosthesis, the hardening step is generally completed prior to changing the topography of the material. Changing the topography of the material can be accomplished in various ways, such as carving or manual manipulation using hand held instruments, or by machine or computer aided apparatus, such as a CAD/CAM milling machine in the case of prostheses and mill blanks. Optionally, a finishing step can be performed to polish, finish, or apply a coating on the dental material.

The following examples are given to illustrate, but not limit, the scope of this invention. Unless otherwise indicated, all parts and percentages are by weight.

TEST METHODS

Average Particle Diameter Determination

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50–100 particles can be measured and an average diameter is determined.

Diametral Tensile Strength (DTS) and Compressive Strength (CS) Testing

ADA ("American Dental Association") specification No. 9 and ADA specification No. 27 respectively of ISO-test procedure 4049 (1988) were followed for all DTS and CS testing. Specifically, for determination of compressive strength ("CS") and diametral tensile strength ("DTS"), the composition was packed into a 4 mm inside diameter glass tube, capped with silicone rubber plugs and axially compressed at about 0.28 MPa for 15 minutes, then light cured for 80 seconds by exposure to two oppositely-disposed Visilux 2™ (3M Co, St. Paul, Minn.) units. Each sample was then irradiated for 90 seconds using a Dentacolor XS unit (Kulzer, Inc., Germany). Cured samples were cut on a diamond saw to form cylindrical plugs 8 mm long for measurement of CS and 2 mm long for measurement of DTS. The plugs were stored in distilled water at 37° C. for 24 hours. CS and DTS values for each composition were measured using an Instron™ (Instron 4505, Instron Corp. Canton, Mass.).

The compressive strength (CS) of these samples was tested on an Instron with 10 kN load cell. A total of 5 cylinders of cured composite with about 8 mm length and 4 mm diameter were prepared.

The Diametral Tensile Strength (DTS) of these samples was tested on an Instron with 10 kN load cell. A total of 5 cylinders of cured composite with about 2 mm length and 4 mm diameter were prepared.

Visual Opacity and Radiopacity Testing

Disc-shaped 1 mm thick by 20 mm diameter samples of the composite were cured by exposing them to illumination from an Visilux 2™ (3M Co, St. Paul, Minn.) curing light for 60 seconds on each side of the disk at a distance of 6 mm. The cured composite samples were then evaluated for visual opacity and radiopacity as follows.

Cured composite samples were measured for direct light transmission by measuring transmission of light through the thickness of the disk using a MacBeth transmission densitometer Model TD-903 equipped with a visible light filter, available from MacBeth (MacBeth, Newburgh, N.Y.).

For radiopacity evaluation, the procedure used followed the ISO-test procdeure 4049 (1988). Specifically, cured composite samples were exposed to radiation using a Gendex GX-770 dental X-ray (Milwaukee, Wis.) unit for 0.73 seconds at 7 milliamps and 70 kV peak voltage at a distance of about 400 millimeters. The X-ray negative was developed using a Air Techniques Peri-Pro automatic film processor. (Hicksville, N.Y.).

Crystallite Particle Size and Crystal Form Content

Particle size of dried zirconia sample from U.S. Application Ser. No. 09/428,374 was reduced by hand grinding using an agate mortar and pestle. A liberal amount of the sample was applied by spatula to a glass microscope slide on which a section of double coated tape had been adhered and pressed into the adhesive on the tape by forcing the sample against the tape with the spatula blade. Excess sample was removed by scraping the sample area with the edge of the spatula blade, leaving a thin layer of particles adhered to the adhesive. Loosely adhered materials remaining after the scraping were remove by forcefully tapping the microscope slide against a hard surface. In a similar manner, corundum (Linde 1.0 μm alumina polishing powder, Lot Number C062, Union Carbide, Indianapolis, Ind.) was prepared and used to calibrate diffractometer for instrumental broadening.

X-ray diffraction scans were obtained from by use of a diffractometer employing copper $K_\alpha$ radiation and Inel CPS120 (Inel Inc, Stratham, N.H.) position sensitive detector registry of the scattered radiation. The detector has a nominal angular resolution of 0.03 degrees (2θ) and received scattering data from 0 to 115 degree (2θ). The X-ray generator was operated at a setting of 40 kV and 10 mA and fixed incident beam slits were used. Data was collected for 60 minutes at a fixed take-off (incident) angle of 6 degrees. Data collections for the corundum standard were conducted on three separate areas of several individual corundum mounts. Data was collected on three separate areas of the thin layer sample mount.

Observed diffraction peaks were identified by comparison to the reference diffraction patterns contained within the ICDD powder diffraction database (sets 1–47, International Center for Diffraction Data, Newton Square, Pa.) and attributed to either cubic/tetragonal (C/T) or monoclinic (M) forms of zirconia. The amounts of each zirconia form were evaluated on a relative basis and the form of zirconia having the most intense diffraction peak was assigned the relative intensity value of 100. The strongest line of each of the remaining crystalline zirconia forms were scaled relative to the most intense line and given a value between 1 and 100.

Peak widths for the observed diffraction maxima due to corundum were measured by profile fitting. The relationship between mean corundum peak widths and corundum peak position (2θ) was determined by fitting a polynomial to these data to produce a continuous function used to evaluate the instrumental breadth at any peak position within the corundum testing range. Peak widths for the observed diffraction maxima due to zirconia were measured by profile fitting observed diffraction peaks. The following peak widths were evaluated depending on the zirconia phase found to be present:

cubic/tetragonal (C/T): (1 1 1)

monoclinic (M): (−1 1 1), and (1 1 1)

Peak widths were found as the peak full width at half maximum (FWHM) having units of degrees using a Pearson VII peak shape model, with $K_{\alpha 1}$ and $K_{\alpha 2}$ wavelength components accounted for, and linear background model. The profile fitting was accomplished by use of the capabilities of the JADE (version 3.1, Materials Data Inc., Livermore, Calif.) diffraction software suite. Sample peak widths were evaluated for the three separate data collections obtained for the same thin layer sample mount.

Sample peaks were corrected for instrumental broadening by interpolation of instrumental breadth values from corundum instrument calibration and corrected peak widths converted to units of radians. Corrected sample peak width (β) were used to evaluate primary crystal (crystallite) size by application of the Scherrer equation. The arithmetic mean of the cubic/tetragonal (C/T) and monoclininc phases (M) were calculated.

β=[calculated peak FWHM−instrumental breadth] (converted to radians)

Crystallite Size $(D) = K\lambda/\beta(\cos\theta)$ where: K=form factor (here 0.9);
λ=wavelength (1.540598 Å);
β=calculated peak width after correction for instrumental broadening (in radians); and
θ=½ the peak position (scattering angle).

Cubic/Tetragonal Mean Crystallite Size =

$$[(D(111))_{area1} + (D(111))_{area2} + (D(111))_{area3}]/3$$

Monoclinic Mean Crystallite Size = $[(D(-111))_{area1} + (D(-111))_{area2} +$ $(D(-111))_{area3} + (D(111))_{area1} + (D(111))_{area2} + (D(111))_{area3}]/6$ The crystallite size is reported in the format:

[C/T crystallite size](parts C/T)+[M crystallite size](parts M)

Weighted average=[(% C/T)(C/T size)+(% M)(M size)]/100 where: % C/T=the percent crystallinity contributed by the cubic and tetragonal crystallite content of the $ZrO_2$ sol;
C/T size=the size of the cubic and tetragonal crystallites;
% M=the percent crystallinity contributed by the monoclinic crystallite content of the $ZrO_2$ sol; and
M size=the size of the monoclinic crystallites.

Crystallinity Index

Particle size of the phase standard (zirconium oxide, calcium stabilized Z-1083 Lot Number 173077-A-1, CERAC Inc, Milwaukee, Wis.) was reduced by ball milling and/or hand grinding using a boron carbide mortar and pestle to pass 325 mesh sieve. Individual mixtures were prepared consisting of 0.400 grams of sample and 0.100 grams of mass standard, a material incorporated into samples being evaluated for crystallinity index to normalize X-ray intensity values based on amount of material present in a sample. Tungsten metal powder (<3 μm) was the mass standard used. Mixtures of the samples were blended under ethanol using an agate mortar and pestle and allowed to dry under flowing nitrogen. A similar mixture composed of the phase standard was also prepared to serve as the crystallinity index reference. The dried mixtures were removed from the mortar and pestle by spatula and fine brush and subsequently transferred to individual sample containers. Portions of each sample were prepared as ethanol slurries on sample holders containing flush mounted glass inserts. Multiple X-ray diffraction scans (a minimum or 10 scans for both sample and standard) were obtained from each sample and phase standard mixture by use of a vertical Bragg-Bretano diffractometer (constructed by Philips Electronic Instruments, Mahwah, N.J.) employing copper $K_\alpha$ radiation, variable incident slit, fixed exit slit, graphite diffracted beam monochromator, and proportional counter registry of the scattered radiation. Scans were conducted from 25–55 degree (2θ) employing a 0.04 degree step size. A 8 second dwell time was used for standard mixture while a 20 second dwell time was employed for sample mixtures to improve counting statistics. The X-ray generator (Spellman High Voltage Electronics Corporation, Hauppage, N.Y.) was operated at a setting of 40 kV and 20 mA. Peak areas for the observed diffraction maxima due to zirconia and tungsten phases were measured by profile fitting observed diffraction peaks within the 25–55 degree (2θ) scattering angle range. The following peak areas were evaluated depending on the zirconia phase found to be present:

cubic (C) (1 1 1), (2 0 0), and (2 2 0)
tetragonal (T) (1 0 1), (0 0 2)/(1 1 0), and (1 1 2)/(2 0 0)
monoclinic (M) (−1 1 1), (1 1 1), (0 0 2), (0 2 0), and (2 0 0)

The X-ray scattering of internal mass standard was evaluated by measurement of cubic tungsten (1 1 0) peak area. A Pearson VII peak shape model and linear background model were employed in all cases. The profile fitting was accomplished by use of the capabilities of the JADE (version 3.1, Materials Data Inc. Livermore, Calif.) diffraction software suite. The peak areas of zirconia peaks outlined above were summed to produce a total zirconia scattered intensity value [(Zirconia Area)$_{sample}$] for each sample as well as standard [(Zirconia Area)$_{standard}$]. These total zirconia scattered intensity values were divided by respective cubic tungsten (1 1 0) peak areas to produce the ratio [$R_{sample}$] for each sample as well as the phase standard [$R_{standard}$]. The arithmetic mean of $R_{sample}$ and $R_{standard}$ are calculated using individual values obtained from the multiple runs of sample and standard, respectively. The crystallinity index [$X_c$] for each sample was calculated as the ratio of $R_{sample(mean)}$ to $R_{standard(mean)}$.

$R_{sample(i)} = [(\text{Total Zirconia Area})_{sample}]/[(\text{Tungsten Area})_{sample}]$ $R_{standard(i)} = [(\text{Total Zirconia Area})_{standard}]/[(\text{Tungsten Area})_{standard}]$ $R_{sample(mean)} = [\Sigma R_{sample(i)}]/N_{sample}$ where $N_{sample}$ = number of sample scans $R_{standard(mean)} = [\Sigma R_{standard(i)}]/N_{standard}$ where $N_{standard}$ = number standard scans $X_c = R_{sample(mean)}/R_{standard(mean)}$ Photon Correlation Spectroscopy This test was used to determine the particles size of suitable heavy metal oxides in a sol. The weight average mean particle diameter of the zirconia particles was determined by Photon Correlation Spectroscopy using a Coulter N4 Submicron Particle Sizer (available from Coulter Corporation, Miami Fla.). Dilute zirconia sol samples were filtered through a 0.45 μm filter using syringe-applied pressure into a glass cuvette. The remaining volume of the cuvette was filled with water, covered, and repeatedly inverted to remove air bubbles. The cuvette was wipe down to remove fingerprints and dust prior to taking any measurements. Light scattering intensity was measured to ensure that an appropriate concentration of sol was sampled. If the intensity was too high, a portion of the cuvette's contents was removed and the remaining contents diluted with water. If the intensity was too low, several more drops of filtered sol were added to the sample and the solution mixed by repeatedly inverting the cuvette. Prior to starting data acquisition the temperature of the sample chamber was allowed to equilibrate for 5 minutes at 25° C. The supplied software was used to do a SDP analysis (1.0 nm–1000 nm) with an angle of 90°. The analysis was performed using 25 data bins. The following values were used in the calculations: refractive index of water=1.333, viscosity of water 0.890 cP, and referactive index for zirconia particles=1.9. Data acquisition immediately ensued for a period of 3:20 minutes. The reported PCS number is the mean diameter based on weight analysis that results from this procedure.

ABBREVIATIONS/DEFINITIONS

| Abbreviations as used in Examples | Description and/or Trade Name | Supplier |
|---|---|---|
| BISEMA6 | ethoxylated (6 mole ethylene oxide) bisphenol A dimethacrylate | Sartomer CD541, Sartomer (Exton, PA) |
| UDMA | Diurethane dimethacrylate, CAS No. 41137-60-4 commercially available as Rohamere 6661-0 | Rohm Tech, Inc. (Malden, MA) |
| BisGMA | 2,2-bis[4-(2-hydroxy-3-methacryloyl-oxypropoxy)phenyl]propane | |
| TEGDMA | Triethyleneglycol dimethacrylate | |
| CPQ | Camphorquinone | |
| CD1012 | Sarcat ™ CD1012 | Sartomer, Inc. (Exton, PA) |
| DPI PF6 | Diphenyl Iodonium Hexafluoro-phosphate | |
| EDMAB | Ethyl 4-dimethylaminobenzoate | |
| BHT | 2,6-Di-tert-butyl-4-methylphenol | |
| Norbloc 7966 | (CAS 96478-09-0) 2-(2'-Hydroxy-5'-methacryloxyethylphenyl)-H-benzotriazole | Janssen Pharmaceutica (Titusville, PA) |

-continued

ABBREVIATIONS/DEFINITIONS

| Abbreviations as used in Examples | Description and/or Trade Name | Supplier |
|---|---|---|
| Tinuvin-P | 2-(2H-Benzotriazol-2-yl)-4-methylphenol | Ciba Specialty Chemicals, Inc. (Basel, Switzerland) |
| TFAA | Trifluoroacetic acid | |
| MEEAA | 2-[2-(2-methoxy)ethoxy]ethoxy acetic acid | |
| G6720 | γ-glycidoxypropyltrimethoxy silane | United Chemical Technologies Inc. (Bristol, PA) |
| A174 | γ-methacryloxypropyltrimethoxy-silane | Witco Osi Specialties (Danbury, CT) |
| P0330 | Phenyltrimethoxysilane | United Chemical Technologies Inc. (Bristol, PA) |
| Nalco 1042 | a nitric acid stabilized colloidal silica sol with a pH of about 3.2 and a nominal particle diameter of 20 nm. Solids content is about 35%. | (Nalco, Naperville, IL) |
| Nalco 2329 | a sodium hydroxide stabilized colloidal silica sol with a pH of about 8–9 and a nominal particle diameter of 75 nm. Solids content is about 40%. | (Nalco, Naperville, IL) |
| Silux Plus | Silux Plus ™ Anterior Restorative, 3M ™ | 3M Co. (St. Paul, MN) |
| Z100 | Z100 ™ Restorative, 3M ™ | 3M Co. (St. Paul, MN) |
| Methoxy-propanol | Methoxy-2-propanol | Aldrich (Milwaukee, WI) |
| Scotchbond | Scotchbond ™ Multi-Purpose Dental Adhesive System, 3M ™ | 3M Co. (St. Paul, MN) |
| Heloxy 48 | Heloxy ™ trimethyolpropane triglycidylether | Shell Chemical Company (Houston, TX) |
| GY-281 | Araldite ™ GY-281 | Cibe Geigy Corp. (Hawthorne, NY) |
| UVR-6105 | Cyracure ™ UVR-6105 | Union Carbide Inc. (Danbury, CT) |
| Zirconia Sol | U.S. Pat. No. 5037579, an aqueous solution with 33% ZrO2 | |
| OX-50 | Fumed Silica | Degussa (Hanau, Germany) |

Preparatory Examples

| Constituent | PBW |
|---|---|
| Resin A | |
| bisGMA | 48.58 |
| TEGDMA | 49.57 |
| EDMAB | 0.6 |
| CPQ | 0.25 |
| Tinuvin-p | 0.98 |
| Resin B | |
| bisGMA | 24.18 |
| UDMA | 33.85 |
| bisEMA6 | 33.85 |
| TEGDMA | 4.84 |
| CPQ | 0.2 |
| DPIHFP | 0.5 |
| EDMAB | 1.0 |
| BHT | 0.1 |
| Norbloc 7966 | 1.5 |

Filler A: Fumed Silica

Treated fumed silica OX-50 (DeGussa, Hanau, Germany) was made as follows: a solution of 3312 g MeOH and 720 g deionized water was premixed for 1 minute. Glacial Acetic Acid, 1024 g, was slowly added to the water followed by 4968 g A-174 silane. The above solution was mixed for 1 hour. At the end of the hydrolysis step, the solution was clear. The solution was used within 30 minutes after hydrolysis. The above solution and 20700 g OX-50 powder were blended for approximately 40 minutes and the treated filler was immediately discharged into drying trays, and was dried at 67° C. for 3.75 hours and then another 1.25 hours at 100° C. The dried filler was screened through a 74 μm nylon screen in a vibratory screener (Vortisiv V/S 10010, Salem, Ohio).

Filler B: Nano-sized Zirconia

Filler B was prepared by mixing together a 14.95 g MEEAA to 210 g of Zirconia Sol of U.S. Pat. No. 5,037,579. Average particle diameter of the zirconia was determined using Photon Correlation Spectroscopy (PCS) described above and was found to be about 60 nm. Thorough mixing for two minutes yielded a homogenous mixture. A solution of 24.36 g of PAMA in 25 g of ethanol was then added to the beaker. The contents were mixed thoroughly using a magnetic stir bar for 60 minutes followed by spray-drying using a Buchi spray drier (Buchi/Brinkmann Mini Spray Dryer Model 190, Brinkmann Instruments, Inc. Westbury, N.Y.) at 200° C. inlet temperature and 85–100° C. outlet temperature.

Filler C: Nano-sized Silica

Filler C was prepared by thoroughly mixing 250 g Nalco 2329, 281.0 g methoxy-2-propanol and 3.72 g of A174. The Nalco 2329 was weighed into a 2 L beaker. The alcohol and silane were weighed into a 1 L beaker and mixed together. The alcohol solution was added to the silica sol slowly with swirling (1–2 min). The resultant mixture was reacted at 80° C. for 16 hr to produce a modified silica sol. A 1 kg portion of water was added to the modified silica sol. This mixture was spray-dried using a Buchi spray drier at 200° C. inlet temperature and 85–100° C. outlet temperature.

EXAMPLE 1

Two dental materials, 1A and 1B, were made with 67% Filler A or Filler C mixed thoroughly into 33% Resin A respectively. The viscosity of the materials was measured using a controlled strain rheometer (model ARES, Rheometric Scientific, N.J.). Material samples were placed in between two parallel plates (25 mm diameter) at a gap of 1 mm. Viscosity measurements were performed at shear rates starting from 0.0125 s$^{-1}$ to 0.0937 s$^{-1}$ in eight logarithmically-spaced shear rate steps.

Shear thinning behaviors were generally absent when the fumed silica, Filler A, was solely used as the filler for the dental material. In contrast, shear thinning behaviors were observed when the dental material contained Filler C.

TABLE 1

| Rate (1/s) | Example 1A (Filler A) units: Poise | Example 1B (Filler C) units: Poise |
| --- | --- | --- |
| 0.0125 | 42220.5 | 2404200 |
| 0.0166 | 56835 | 2239950 |
| 0.0222 | 79790.5 | 1805350 |
| 0.0296 | 118215 | 1393450 |
| 0.0395 | 110630 | 1047085 |

TABLE 1-continued

| Rate (1/s) | Example 1A (Filler A) units: Poise | Example 1B (Filler C) units: Poise |
| --- | --- | --- |
| 0.0527 | 90015 | 768925 |
| 0.0702 | 72276.5 | 562270 |
| 0.0937 | 57961 | 404945 |

EXAMPLE 2

Filler C, in varying amounts, was mixed into Resin B, as shown in Table 7, to make 3 different materials. The materials were hardened and their mechanical properties were evaluated according to DTS, VO, and CS methods previously described.

TABLE 2

| Mechanical Properties | Example 2A 35% Resin B 65% Filler C | Example 2B 30% Resin B 70% Filler C | Example 2C 27% Resin B 73% Filler C | Comparative Microfill Silux Plus ™ |
| --- | --- | --- | --- | --- |
| DTS (MPa) | 68.97 | 78.62 | 70.34 | 49.52 |
| CS (Mpa) | 438.84 | 448.46 | 408.48 | 358.12 |
| VO | 0.16 | 0.14 | 0.14 | 0.26 |

EXAMPLE 3

To make the fillers for examples 3A–3D, various amounts of A174 (silane), as listed in Table 3, were added to a mixture of 250 g of the Nalco 2329 sol and 281 g methoxy propanol. The Nalco 2329 was weighed into a 2 L beaker. The alcohol and silane were weighed into a 1 L beaker and mixed together. The alcohol solution was added to the silica sol slowly with swirling (1–2 min) and maintained at a temperature of about 80° C. for about 16 hours. The four silane-treated silica sols were solvent-exchanged by mixing each silane-treated silica sol with 69 g of Resin A and heating the modified organic sol in an oven at 85–90° C. for 4 hours.

Filler B was thoroughly mixed with each of the four modified organic sols to make materials with a final composition for each material of 31.5 pbw Resin A, 45.5 pbw of silane-treated silica and 23 pbw Filler B. The four materials were hardened according to the Visual Opacity and DTS methods previously described. The Visual Opacity and the DTS data are illustrated in Table 3.

TABLE 3

| | Example 3A | Example 3B | Example 3C | Example 3D |
| --- | --- | --- | --- | --- |
| Weight of A174 Silane per 100 g SiO2 | 1.86 | 3.72 | 7.44 | 11.16 |
| Visual opacity | 0.30 | 0.26 | 0.24 | 0.24 |
| DTS (Mpa) | 63.86 | 67.59 | 65.79 | 62.14 |

EXAMPLE 4

Scotchbond™ adhesive (3M Co., St. Paul, Minn.) was combined and thoroughly mixed with Filler C to make Example 4A. The same adhesive was combined and thoroughly mixed with Filler B and C to make Example 4B. Table 4 provides the concentrations of the components for each material.

Adhesive strength to dentin and enamel of the two adhesives was evaluated by the following procedure. Five bovine teeth per adhesive composition of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 600 silicon carbide paper-backed abrasive on the lapidary wheel.

The polished teeth were stored in distilled water, and used for testing within 2 hours after polishing. The polished teeth were removed from the water and blotted dry. Using a Scotchbond™ kit 7540S (3M Co., St. Paul, Minn.), Scotchbond™ etchant was painted onto each of the polished tooth surfaces with a brush, allowed to stand for 15 seconds, rinsed with distilled water and then blotted dry. A single drop of Scotchbond™ primer was painted onto each of the polished tooth surfaces with a brush and immediately blown dry with compressed air for 5 sec.

Adhesives 4A thru 4B were painted onto each of the tooth surfaces, and hardened using a 10-second irradiation with a Visilux 2™ dental curing light. Previously prepared molds made from a 2-mm thick TEFLON (E.I. Dupont Nemours, Wilmington, Del.) sheet with a 4 mm diameter hole through the sheet were clamped to each prepared tooth so that the central axis of the hole in the mold was normal to the tooth surface. The hole in each mold was filled Z100 and hardened with a Visilux 2™ dental curing light using a 40-second irradiation.

The teeth and molds were stored in distilled water at 37C for approximately 24 hours. The molds were then carefully removed from the teeth, leaving a molded button of restorative attached to each tooth.

Adhesive strength was evaluated by mounting the acrylic disk in a holder clamped in the jaws of an Instron apparatus with the polished tooth surface oriented parallel to the direction of pull. A loop of orthodontic wire (0.44 mm diameter) was placed around the restorative button adjacent to the polished tooth surface. The ends of the orthodontic wire were clamped in the pulling jaw of the Instron apparatus, thereby placing the bond in shear stress. The bond was stressed until it (or the dentin or button) failed, using a crosshead speed of 2 mm/min. Good adhesion was observed.

TABLE 4

| Composition | Enamel | | Dentin | |
|---|---|---|---|---|
| | Adhesion Strength (Mpa) | STDev (MPa) | Adhesion Strength (MPa) | STDev (MPa) |
| 4A 62% Scotchbond/ 38% Filler C | 23.4 | 6.9 | 21.9 | 6.4 |
| 4B 50% Scotchbond/ 38% Filler C/ 12% Filler B | 27.9 | 4.3 | 18.5 | 3.4 |

EXAMPLE 5

The sols, methoxypropanol and silanes, as listed in Table 5 for 5A–5D were added to a round-bottom flask and put on a rotary evaporator. For 5A and 5B, the mixtures were mixed at 45° C. for approximately 2 hours. For 5C and 5D, the mixtures were mixed at 90° C. for approximately 1 hour. For 5E, the mixture was stirred at 45° C. for approximately 1 hour.

For 5A, a vacuum (approximately 400 mm Hg) was pulled on the sample to remove most of the water until there was approximately 109 g of mixture remaining. The portion of UVR-6105, as listed in Table 5, was added to the mixture of alcohol, silane, and silica and was allowed to rotate on the rotary evaporator until the epoxy was dissolved. The vacuum was again applied and the temperature was increased to 65° C. Vacuum was pulled for approximately 1 hour, at which point no residual condensate was observed on the collecting coils of the rotary evaporator. Material 5A contained approximately 40% silica by weight and was transparent upon visual inspection.

For 5B, a vacuum (approximately 400 mm Hg) was pulled on the sample to remove most of the water until there was approximately 67 g of mixture remaining. The portion of UVR-6105, as listed in Table 5, was added to the mixture of alcohol, silane, and silica and was allowed to rotate on the rotary evaporator until the epoxy was dissolved. The vacuum was again applied. Vacuum was pulled for approximately 1 hour, at which point no residual condensate was observed on the collecting coils of the rotary evaporator. This material contained approximately 52% silica by weight and was transparent upon visual inspection.

For 5C, a vacuum (approximately 400 mm Hg) was pulled on the sample to remove most of the water until there was approximately 109 g of mixture remaining. The portions of UVR-6105 and Heloxy 48 and GY281, as listed in Table 5, were added to the mixture of alcohol, silane, and silica and was allowed to rotate on the rotary evaporator until the epoxies were dissolved. The vacuum was again applied. Vacuum was pulled for approximately 1 hour, at which point no residual condensate was observed on the collecting coils of the rotary evaporator. This material contained approximately 50.8% silica by weight and was transparent upon visual inspection.

For 5D, a vacuum (approximately 400 mm Hg)was pulled on the sample to remove most of the water until there was approximately 120 g of mixture remaining. The portions of UVR-6105 and GY281, as listed in Table 5, were added to the mixture of alcohol, silane, and silica and was allowed to rotate on the rotary evaporator until the epoxies were dissolved. The vacuum was again applied at a temperature of 55° C. Vacuum was pulled for approximately 1 hour, at which point the temperature was increased to 90° C. for 5 minutes. No residual condensate was observed on the collecting coils of the rotary evaporator at this point. This material contained approximately 40.0% silica by weight and was transparent upon visual inspection.

For each of the materials, an initiator component of 2 wt % CD1012; 0.1 wt % EDMAB; and 0.6 wt % camphorquinone by weight of the epoxy resin component was thoroughly mixed into the material. Materials 5A–5D were exposed to a 3M Visilux 2™ Dental Curing Light for 10–20 seconds. Material 5E was exposed to a 3M Visilux 2™ Dental Curing Light for 20 seconds. The visual appearance and determination of whether hardening of each of the materials took place after exposure to a 3M Visilux 2™ are presented in Table 6.

TABLE 5

| Material | Sol Nalco 1042 (g) | Methoxy Propanol (g) | Silane G6720 (g) | Silane P0330 (g) | Epoxy UVR-6105 (g) | Epoxy Heloxy 48 (g) | Epoxy GY281 (g) |
|---|---|---|---|---|---|---|---|
| 5A | 100.6 | 102.0 | 10.3 |  | 41.7 |  |  |
| 5B | 101.0 | 100.5 | 6.1 |  | 25.5 |  |  |
| 5C | 103.0 | 106.8 |  | 3.5 | 12.1 | 6.7 | 12.4 |
| 5D | 100.6 | 101.4 | 1.8 | 1.8 | 24.0 |  | 24.3 |

TABLE 6

| Material | Visual Appearance | Hardening of Material |
|---|---|---|
| 5A | Clear | Yes |
| 5B | Clear | Yes |
| 5C | Clear | Yes |
| 5D | Clear | Yes |

What is claimed is:

1. A filler in a dry powder form comprising non-aggregated, non-fumed silica particles having a silane treated surface, wherein the silica particles have an average diameter of less than about 200 nm.

2. The filler of claim 1 wherein the silica particles are capable of being dispersed in a medium to form a dispersion of non-agglomerated, non-aggregated, non-fumed silica particles.

3. A method of preparing a filler in a dry powder form comprising drying a volatile liquid dispersion of non-aggregated, non-fumed silica particles having a silane treated surface, wherein the silica particles have an average diameter of less than about 200 nm.

4. The method of claim 3 wherein the drying comprises spray drying the dispersion.

5. The method of claim 3 wherein the dispersion of silica particles comprises non-agglomerated, non-aggregated, non-fumed silica particles.

6. The method of claim 3 wherein the volatile liquid comprises water.

7. The method of claim 6 wherein the volatile liquid further comprises a cosolvent.

8. The method of claim 7 wherein the cosolvent comprises an alcohol.

9. The method of claim 3 further comprising treating the surface of non-aggregated, non-fumed silica particles having an average diameter of less than about 200 nm and dispersed in a volatile liquid with a silane to form a volatile liquid dispersion of non-aggregated, non-fumed silica particles having a silane treated surface.

10. A filler in a dry powder form prepared by a method comprising drying a volatile liquid dispersion of non-aggregated, non-fumed silica particles having a silane treated surface, wherein the silica particles have an average diameter of less than about 200 nm.

11. A method of preparing a composition comprising dispersing in a hardenable resin a filler in a dry powder form, the filler comprising non-aggregated, non-fumed silica particles having a silane treated surface, wherein the silica particles have an average diameter of less than about 200 nm.

12. The method of claim 11 wherein dispersing forms a dispersion of non-agglomerated, non-aggregated, non-fumed silica particles in the resin.

13. The method of claim 11 further comprising dispersing fumed silica in the hardenable resin.

14. A method of preparing a composition comprising dispersing in a hardenable resin a filler in a dry powder form, the filler comprising non-aggregated, non-fumed silica particles having a silane treated surface and having an average diameter of less than about 200 nm to form a dispersion in the hardenable resin of non-agglomerated, non-aggregated, non-fumed silica particles having an average diameter of less than about 200 nm, wherein the composition comprises at least about 40% by weight non-agglomerated, non-aggregated, non-fumed silica particles.

15. The method of claim 14 wherein the composition comprises at least about 50% by weight non-agglomerated, non-aggregated, non-fumed silica particles.

16. The method of claim 14 wherein the composition, after hardening, has a visual opacity value of no greater than about 0.4.

17. The method of claim 14 wherein the composition, after hardening, has a visual opacity value of no greater than about 0.35.

18. The method of claim 14 wherein the composition, after hardening, has a visual opacity value of no greater than about 0.25.

19. The method of claim 14 wherein the hardenable resin is selected from the group consisting of acrylates, methacrylates, epoxies, and mixtures thereof.

20. The method of claim 14 further comprising adding an initiator to the hardenable resin.

21. The method of claim 14 further comprising dispersing a heavy metal oxide in the hardenable resin.

22. The method of claim 21 wherein the heavy metal oxide is selected from the group consisting of zirconium oxide, cerium oxide, tin oxide, yttrium oxide, strontium oxide, barium oxide, lanthanum oxide, zinc oxide, ytterbium oxide, bismuth oxide and mixtures thereof.

23. The method of claim 21 wherein the heavy metal oxide is a cubic or tetragonal zirconium oxide.

24. The method of claim 14 wherein the composition forms a material selected from the group consisting of dental restoratives, dental adhesives, casting materials, dental cements, dental sealants, and dental coatings.

25. A method of preparing a dental article comprising:
dispersing in a hardenable resin a filler in a dry powder form, the filler comprising non-aggregated, non-fumed silica particles having a silane treated surface and having an average diameter of less than about 200 nm to form a composition comprising a dispersion in the hardenable resin of non-agglomerated, non-aggregated, non-fumed silica particles having an average diameter of less than about 200 nm, wherein the composition comprises at least about 40% by weight non-agglomerated, non-aggregated, non-fumed silica particles; and
hardening the composition to fabricate a dental article selected from the group consisting of dental mill blanks, dental prostheses, orthodontic devices, artificial crowns, anterior fillings, posterior fillings, and cavity liners.

26. The method of claim 25 further comprising changing the topography of the composition before hardening the composition.

27. A method of preparing a composition comprising:
dispersing in a hardenable resin a filler in a dry powder form, the filler comprising non-aggregated, non-fumed silica particles having a silane treated surface and having an average diameter of less than about 200 nm to form a dispersion in the hardenable resin of non-agglomerated, non-aggregated, non-fumed silica particles having an average diameter of less than about 200 nm; and dispersing fumed silica in the hardenable resin, wherein the composition, after hardening, has a visual opacity value of no greater than about 0.4.

28. The method of claim 27 wherein the composition comprises at least about 40% by weight non-agglomerated, non-aggregated, non-fumed silica particles.

* * * * *

UNITED STATES PATENT AND TRADEMARK OFFICE
CERTIFICATE OF CORRECTION

PATENT NO. : 6,899,948 B2
DATED : May 31, 2005
INVENTOR(S) : Zhang, Xiaodong

It is certified that error appears in the above-identified patent and that said Letters Patent is hereby corrected as shown below:

Column 2,
Lines 1-2, delete "theological" and insert -- rheological --, therefor.

Column 3,
Line 27, delete "(Theological)" and insert -- (rheological) --, therefor.

Column 10,
Line 29, delete "application No. 5520QUSA5A" and insert -- Application No. 55200USA5A --, therefor.

Column 13,
Line 67, after "acrylate" delete "." and insert -- , --, therefor.

Column 19,
Line 41, delete "DEN431" and insert -- DEN-431 --, therefor.
Line 42, delete "DEN438" and insert -- DEN-438 --, therefor.

Column 22,
Line 7, delete "heron" and insert -- herein --, therefor.
Line 34, delete "bejoined" and insert -- be joined --, therefor.
Line 37, delete "-COOR2" and insert -- $COOR^2$ --, therefor.

Column 23,
Line 26, delete "rinand" and insert -- rings, and --, therefor.

UNITED STATES PATENT AND TRADEMARK OFFICE
CERTIFICATE OF CORRECTION

PATENT NO. : 6,899,948 B2
DATED : May 31, 2005
INVENTOR(S) : Zhang, Xiaodong

It is certified that error appears in the above-identified patent and that said Letters Patent is hereby corrected as shown below:

Column 29,
Line 2, delete "-[Total Zirconia Area)$_{standard}$]" and insert -- [(Total Zirconia Area) $_{standard}$] --, therefor.
Line 25, delete "wipe" and insert -- wiped --, therefor.

Column 30,
Line 43, Table Column 3, delete "Degussa" and insert -- DeGussa --, therefor.

Signed and Sealed this

Twenty-third Day of August, 2005

JON W. DUDAS
*Director of the United States Patent and Trademark Office*